(12) United States Patent
Vaisberg et al.

(10) Patent No.: US 7,016,787 B2
(45) Date of Patent: Mar. 21, 2006

(54) CHARACTERIZING BIOLOGICAL STIMULI BY RESPONSE CURVES

(75) Inventors: Eugeni A. Vaisberg, Foster City, CA (US); Donald R. Oestreicher, Cupertino, CA (US); Cynthia L. Adams, Berkeley, CA (US)

(73) Assignee: Cytokinetics, Inc., So. San Francisco, CA (US)

( * ) Notice: Subject to any disclaimer, the term of this patent is extended or adjusted under 35 U.S.C. 154(b) by 0 days.

(21) Appl. No.: 09/789,595

(22) Filed: Feb. 20, 2001

(65) Prior Publication Data

US 2002/0155420 A1 Oct. 24, 2002

(51) Int. Cl.
*G01N 33/48* (2006.01)
*G06K 9/00* (2006.01)

(52) U.S. Cl. .......................... 702/19; 382/128; 382/133
(58) Field of Classification Search .................. 702/19; 382/128, 133; 435/6, 7.23
See application file for complete search history.

(56) References Cited

U.S. PATENT DOCUMENTS

| | | | |
|---|---|---|---|
| 4,818,710 | A | 4/1989 | Sutherland et al. |
| 4,922,092 | A | 5/1990 | Rushbrooke et al. |
| 4,959,301 | A | 9/1990 | Weaver et al. |
| 4,965,725 | A | 10/1990 | Rutenberg |
| 5,016,283 | A | 5/1991 | Bacus et al. |

(Continued)

FOREIGN PATENT DOCUMENTS

| | | |
|---|---|---|
| EP | 0317139 | 4/1998 |
| WO | 93/21511 | 10/1993 |
| WO | WO 95/22749 | 8/1995 |
| WO | 96/09605 | 3/1996 |
| WO | WO97/11094 | 3/1997 |

(Continued)

OTHER PUBLICATIONS

Stearns et al., Interleukin 10 (IL–10) Inhibition of Primary Human Prostate Cell–Induced Angiogenesis: IL–10 Stimulation of Tissue Inhibitor of Metalloproteinase–1 and Inhibition of Matrix Metalloproteinase (MMP)–2/MMP–9 Secretion, Clinical Research, vol. 5, 189–196, Jan. 1999.
Russ, J. C. "The Image Processing Handbook," Second Edition, Boca Raton, CRC Press, 1995, pp. 457–461 and 469–474.
Lu et al., Hierarchical Shape Recognition Using Polygon Approximation and Dynamic Alignment, IEEE Paper CH2561–9, vol. 2, pp. 976–979, 1988.
Cormack et al., FACS–optimized mutants of the green fluorescent protein (GFP), *Gene. 173* (1996) 33–38.
Craig et al., "IS hsp 70 the cellular thermometer?" TIBS 16, *Apr. 1991*.

Cubitt et al., "Understanding, improving and using green fluorescent proteins," Elsevier Science Ltd., 0968–00004/95, Nov. 1995.
Dobson et al., "Dynamics of insulin–stimulated translocation of GLUT4 in single living cells visualized using green fluorescent protein," Federation of European Biochemical Societies, 1996.
Georget et al., "Trafficking of the androgen receptor in living cells with fused green fluorescent protein—androgen receptor," Molecular and Cellular Endocrinology 129 (1997) 17–26.
Lippincott–Schwartz, "Insights into secretory and endocytic membrane traffic using green fluorescent protein chimeras," *Current Opinion in Neurobiology*, vol. 7, pp. 631–639 1997.
Misteli, Tom and Spector, David L., "Applications of the green fluorescent protein in cell biology and biotechnology", 1997, *Nature Biotechnology*, vol. 15, pp. 961–964.
Palm, Gottfried J. et al., "The structural basis for spectral variations in green fluorescent protein", 1997, *Nature Structural Biology*, vol. 4, No. 5, pp. 361–365.
Sakai, Kenji et al., "Purification and characterization of N–acyl–D–glutamate deacylase from *Alcaligenes xylosoxydans* A–6", 1991, *FEBS Letters*, vol. 289, No. 1, pp. 44–46.
Shulga, Nataliya et al., "In Vivo Nuclear Transport Kinetics in *Saccharamyces cerevisiae*: A Role for Heat Shock Protein 70 during Targeting and Translocation", 1996, *The Journal of Cell Biology*, vol. 135, No. 2, pp. 329–339.
Tarasova, Nadya I. et al., "Visualization of G Protein–coupled Receptor Trafficking with the Aid of the Green Fluorescent Protein", *The Journal of Biological Chemistry*, vol. 272, No. 23, Issue of Jun. 6, pp. 14817–14824.
Welsh, Stephen and Kay, Steve A., "Reporter gene expression for monitoring gene transfer", 1997, *Current Opinion in Biotechnology*, vol. 8, pp. 617–622.
Boland, Micheael et al., Automated Recognition of Patterns Characteristic of Subcellular Structures in Fluorescence Microscopy Images, Rapid Communications, 1998 Cytometry, 33:366–375.

(Continued)

*Primary Examiner*—Marjorie A. Moran
*Assistant Examiner*—Lori A. Clow
(74) *Attorney, Agent, or Firm*—Beyer, Weaver & Thomas LLP

(57) ABSTRACT

A method for generating stimulus response curves (e.g., dose response curves) shows how the phenotype of one or more cells change in response to varying levels of the stimulus. Each "point" on the curve represents quantitative phenotype for cell(s) at a particular level of stimulus (e.g., dose of a therapeutic). The quantitative phenotypes are multivariate phenotypic representations of the cell(s). They include various features of the cell(s) obtained by image analysis. Such features often include basic parameters obtained from images (e.g., cell shape, nucleus area, Golgi texture) and/or biological characterizations derived from the basic parameters (e.g., cell cycle state, mitotic index, etc.). The stimulus response curves may be compared to allow classification of stimuli and identify subtle differences in related stimuli. To facilitate the comparison, it may be desirable to present the response curves in a principal component space.

47 Claims, 18 Drawing Sheets

U.S. PATENT DOCUMENTS

| | | |
|---|---|---|
| 5,162,990 A | 11/1992 | Odeyale et al. |
| RE34,214 E | 4/1993 | Carlsson et al. |
| 5,281,517 A | 1/1994 | Bacus et al. |
| 5,287,272 A | 2/1994 | Rutenberg et al. |
| 5,326,691 A | 7/1994 | Hozier |
| 5,355,215 A | 10/1994 | Schroeder et al. |
| 5,526,258 A | 6/1996 | Bacus |
| 5,548,661 A | 8/1996 | Price et al. |
| 5,655,028 A | 8/1997 | Soll |
| 5,710,022 A | 1/1998 | Zhu et al. |
| 5,733,721 A | 3/1998 | Hemstreet, III et al. |
| 5,741,648 A | 4/1998 | Hemstreet et al. |
| 5,768,412 A | 6/1998 | Mitsuyama et al. |
| 5,776,748 A | 7/1998 | Singhvi et al. |
| 5,777,888 A | 7/1998 | Rine et al. |
| 5,790,692 A | 8/1998 | Price et al. |
| 5,790,710 A | 8/1998 | Price et al. |
| 5,804,436 A | 9/1998 | Okun et al. |
| 5,856,665 A | 1/1999 | Price et al. |
| 5,893,095 A | 4/1999 | Jain et al. |
| 5,919,646 A | 7/1999 | Okun et al. |
| 5,932,872 A | 8/1999 | Price |
| 5,962,520 A | 10/1999 | Smith et al. |
| 5,976,825 A | 11/1999 | Hochman |
| 5,985,549 A | 11/1999 | Singer et al. |
| 5,989,835 A | 11/1999 | Dunlay et al. |
| 5,991,028 A | 11/1999 | Cabib et al. |
| 5,995,143 A | 11/1999 | Price et al. |
| 6,007,996 A | 12/1999 | McNamara et al. |
| 6,008,010 A | 12/1999 | Greenberger et al. |
| 6,078,681 A | 6/2000 | Silver |
| 6,083,763 A | 7/2000 | Balch |
| 6,103,479 A | 8/2000 | Taylor |
| 6,146,830 A | 11/2000 | Friend et al. |
| 6,169,816 B1 | 1/2001 | Ravkin |
| 6,222,093 B1 | 4/2001 | Marton et al. |
| 6,345,155 B1 | 2/2002 | Tojo et al. |
| 6,615,141 B1 | 9/2003 | Sabry et al. |
| 6,658,143 B1 | 12/2003 | Hansen et al. |

FOREIGN PATENT DOCUMENTS

| | | |
|---|---|---|
| WO | 97/43732 | 11/1997 |
| WO | WO 98/45704 | 10/1998 |
| WO | WO 98/52018 | 11/1998 |
| WO | 99/05323 | 2/1999 |
| WO | WO 99/17116 | 4/1999 |
| WO | WO 99/39184 | 8/1999 |
| WO | WO 99/54494 | 10/1999 |
| WO | WO 00/29984 | 5/2000 |
| WO | WO00/65472 | 11/2000 |
| WO | WO00/70528 | 11/2000 |
| WO | WO0135072 A2 | 5/2001 |
| WO | WO02/50512 | 6/2002 |

OTHER PUBLICATIONS

Wang et al., "Immunolocalization of 6", His–tagged pr in CHO cells with anti–His antibodies, Dec. 1999.

Kapur et al., "Design and Fabrication of Spatially Controlled Miniatutrized Organ Systems from Stem Cells," U.S. Appl. No. 60/127,339, filed Apr. 1, 1999.

Adams et al., "Cell Patterning on Glass and Polymeric Substrates" U.S. Appl. No. 60/138,119, filed Jun. 7, 1999.

Cseke, I., "A fast segmentation scheme for white blood cell images" (1992) IEEE, pp. 530–533.

Hartwell et al., "Integrating genetic approaches into the discovery of anticancer drugs," (1997) Science 278:1064–1068.

Hofland et al., "Role of tumor–derived fibroblasts in the growth of primary cultures of human breast–cancer cells: effects of epidermal growth factor and the somatostatin analogue octreotide" (1995), Int. J. Cancer: 60:93–99.

Ng et al., "Evaluating multi–dimensional indexing structures for images transformed by principal component analysis," Proceedings of SPIE, Bellingham, Spie, US (1996), vol. 2670, pp. 50–61.

Takayama et al., "Patterning cells and their environments using multiple laminar fluid flows in capillary networks," (1999) Proc. Natl., Acad. Sci. USA, 96:5545–5548.

Pauwels et al., "Determination of the Mechanism of Action of Anticancer Drugs by Means of the Computer–Assisted Microscope Image Analysis of Feulgen–Stained Nuclei", J. Pharmacological and Toxicological Methods. 37: 105–115 (1997).

Rubas, et al., "An Integrated Method to Determine Epithelial Transport and Bioactivity of Oral Drug Candidates in Vitro," Pharmaceutical Research, vol. 13, No. 1, (1996) pp 23–27.

Sunblad et al., "The use of image analysis and automation for measuring mitotic index in apical confier meristems", © Oxford University Press 1998, Journal of Experimental Botany, vol. 49, No. 327, pp. 1745–1756.

Uria JA, et al., "Regulation of Collagenase–3 Expression in Human Breast Carcinomas in Mediated by Stromal–Epithelial Cell Interactions", Cancer Res Nov. 1, 1997;57 (21):4882–8, Abstract.

U.S. Appl. No. 60/120,801, Wang et al., filed Feb. 19, 1999.
U.S. Appl. No. 60/142,646, Boyce et al., filed Jul. 6, 1999.
U.S. Appl. No. 60/142,375, Boyce et al., filed Jul. 6, 1999.
U.S. Appl. No. 60/108,291, Boyce et al., filed Nov. 13, 1998.
U.S. Appl. No. 60/110,643, Smith, filed Dec. 1, 1998.
U.S. Appl. No. 60/140,240, Dunlay et al., filed Jun. 21, 1999.

Notification of Transmittal of International Preliminary Examination Report, Int'l Application No. PCT/US02/05553, Filed Feb. 20, 2002, 6 pages.

Mattheakis et al., PCT Search Report for Int'l Application No. PCT/US2004/022970, Int'l Filing Date Jul. 15, 2004, dated Dec. 1, 2004.

Mattheakis et al., PCT Written Opinion for Int'l Application No. PCT/US2004/022970 Int'l Filing Date Jul. 15, 2004.

Towner et al., "Non–Invasive in Vivo Magnetic Resonance Imagig Assessment of Acute Aflatoxin B1 Hapatotoxicity in Rats", BBA—General Subjects, Elsevier Science Publishers, NL, vol. 1475, No. 3, Jul. 26, 2000, pp. 314–320.

Sturgeon et al., "In Vivo Assessment of Microcystin–LR–induced Hepatoxicity in the rat using proton nuclear magnetic rezsonance ($^1$H–NMR) Imaging" BBA—General Subjects, Biochemica et Biophysica Acta 1454 (1999) pp 227–235.

Sakai et al., Rapid and Sensitive Neurotoxicity Test Based on the Morphological Changes of PC12 Cells with Simple Computer–Assisted Image Analysis, Journal of Bioscience and Bioengineering, vol. 90, No. 1, 20–24. 2000.

Hall et al., "Two Methods of Assessment of Methotrexate Hepatotoxicity in Patients with Rheumatoid Arthritis", Annals of the Rheumatic Diseases 1991, vol. 50, No. 7, pp. 471–476.

Molinari et al., "Automated Image Analysis for Monitoring Oxidative Burst in Macrophages", Analytical and Quantitative Cytology and Histology, vol. 22, No. 5, Oct. 2000, pp423–427.

Ancin, Hakan et al., "*Advances in Automated 3–D Image Analysis of Cell Populations Imaged by Confocal Microscopy*", 1996, Cytometry, vol. 25, pp. 221–234.

Malpica, Norberto et al., "*Applying Watershed Algorithms to the Segmentation of Clustered Nuclei*", 1997, Cytometry, vol. 28, pp. 289–297.

Nilsson, Björn et al., "*Segmentation of Dense Leukocyte Clusters*", 2001, IEEE Workshop on Mathematical Methods in Biomedical Image Analysis, Kauai, Hawaii, pp. 221–227.

Legend
Farnesyl transferase (green),
Geranylgeranyltransferase (blue) and
Mitochondrial inhibitors (pink and gray)
(See legend for Figure 3A for additional details)

Legend
Actin inhibitors (red)
Tubulin depolymerizers (purple)
(See legend for Figure 3A for additional details)

Legend
ER-Ca+2 ATPase inhibitors (black)
G protein activators (blue)
Kinase inhibitors (brown and gray)
(See legend for Figure 3A for additional details)

Legend
Red data points are from one run
Blue from a run 3 weeks later

Compounds that have biochemical activity against Cytokinetics' target

Legend
Primary hits (red)
Optimized hits (blue)

Primary hits
The subset of compounds that were identified in the primary screen

Legend
The region of the PCA space that represents the optimal profile for inhibition of a Target

Legend
Zoomed-in figure of the compounds in PCA space in Figure 11.
Primary hits (red)
Secondary analogs (black)
Optimized hits (blue)

CHARACTERIZING BIOLOGICAL STIMULI BY RESPONSE CURVES

CROSS-REFERENCE TO RELATED APPLICATIONS

This application is related to the following co-pending U.S. patent applications, U.S. patent application Ser. No. 09/310,879 by Vaisberg et al., and titled DATABASE METHOD FOR PREDICTIVE CELLULAR BIOINFORMATICS; U.S. patent application Ser. No. 09/311,996 by Vaisberg et al., and titled DATABASE SYSTEM INCLUDING COMPUTER FOR PREDICTIVE CELLULAR BIOINFORMATICS; U.S. patent application Ser. No. 09/311,890, now U.S. Pat. No. 6,743,576, by Vaisberg et al., and titled DATABASE SYSTEM FOR PREDICTIVE CELLULAR BIOINFORMATICS. Each of these applications was filed on May 14, 1999. This application is also related to U.S. patent application Ser. No. 09/729,754, now U.S. Pat. No. 6,876,760, by Vaisberg et al., and titled CLASSIFYING CELLS BASED ON INFORMATION CONTAINED IN CELL IMAGES filed on Dec. 4, 2000. This application is further related to U.S. patent application Ser. No. 09/792,013 (Pulblication No. 20020154798) by Vaisberg et al., and titled EXTRACTING SHAPE INFORMATION CONTAINED IN CELL IMAGES, and U.S. patent application Ser. No. 09/792,012 (Publication No. 20020141631) by Vaisberg et al., and titled IMAGE ANALYSIS OF THE GOLGI COMPLEX, both filed on the same day as the instant application. Each of the above patent applications is incorporated herein by reference for all purposes.

BACKGROUND OF THE INVENTION

The present invention relates to techniques for determining the response of biological cells to varying levels of a particular stimulus. More specifically, the invention relates to response curves derived from multivariate phenotypic data extracted from images of biological cells.

Purified substances having a desirable combination bioactive properties are rare and often difficult to identify. Recent advances in traditional organic chemistry and the development of rapid combinatorial chemistry techniques have increased the number of compounds that researchers can test for a specific biological activity (e.g., binding to a target). Unfortunately, the vast majority of "hits" generated by such techniques do not possess the right combination of properties to qualify as therapeutic compounds. When these substances are subjected to low throughput cellular and animal tests to establish their therapeutic usefulness, they are typically found to fail in some regard. Unfortunately, such tests are time consuming and costly, thus limiting the number of substances that can be tested. In a like regard, the few hits that do possess the right combination of properties avoid recognition until after the throughput tests are conducted. With better early evaluation techniques, such promising candidates could be identified earlier in the development process and put on a fast track to the marketplace.

Various early evaluation techniques are under investigation and some have shown promise. In particular cellular phenotyping technologies employing sophisticated image analysis have proven very useful in characterizing therapeutic chemicals. Such technologies are generally described in WO/00/70528 published on Nov. 23, 2000. These techniques attempt to classify compounds based on phenotypic changes that they induce. From these changes, detailed mechanisms of action can be deduced.

Typically, researchers attempting to classify a new compound based on mechanism of action wish to know how that compound compares to other known therapeutics. Compounds that exhibit similar biological functioning in some regards may exhibit similarity in other regards as well. One difficulty in assessing similarity is that compounds often have greatly varying potencies. In other words, while two different compounds may operate by the same or similar mechanism of action, one compound may operate at a much lower concentration than the other compound. It is difficult to make meaningful comparison of two such compounds until the dose scales of these compounds have been adjusted. To this end, researchers often use dose response curves to compare compounds. These curves show the biological effectiveness of particular drugs over multiple concentrations. The effect of the drug at each different concentration provides the "points" for the dose response curves.

Typically, such dose response curves are limited to a single particular biological parameter (e.g., cell count or expression of a protein). The numeric value of such parameter is provided as a function of concentration for each compound of interest. The resulting curves can be compared to identify similar trajectories. Two compounds having similar trajectories might be expected to operate by the same mechanism of action, depending upon which biological parameter is being considered. Unfortunately, there are significant limits to the value of such comparisons. Most importantly, many different parameters may contribute to a mechanism's signature. So a simple dose response curve may fail to shed light on a mechanism.

While image analysis techniques for characterizing phenotypes can provide many different characteristics of a compound, their full potential has not yet been realized. Particularly, it would be useful if such techniques could be applied to obtain meaningful dose response information for compounds or other stimuli under investigation.

SUMMARY OF THE INVENTION

The present invention provides a method, program code, and apparatus for generating stimulus response curves (e.g., dose response curves) showing how the phenotype of one or more cells change in response to varying levels of the stimulus. Each "point" on the curve represents quantitative phenotype for cell(s) at a particular level of stimulus (e.g., dose of a therapeutic). The quantitative phenotypes are multivariate phenotypic representations of the cell(s). They include various features of the cell(s) obtained by image analysis. Such features often include basic parameters obtained from images (e.g., cell shape, nucleus area, Golgi texture) and/or biological characterizations derived from the basic parameters (e.g., cell cycle state, mitotic index, etc.). The stimulus response curves may be compared to allow classification of stimuli and identify subtle differences in related stimuli. To facilitate the comparison, it may be desirable to present the response curves in a principal component space.

One specific aspect of the invention provides a method for determining the response of cells to multiple levels of a stimulus. The method may be characterized by the following sequence: (a) obtaining feature values which characterize the phenotype of cells exposed to a particular level of the stimulus to produce a "quantitative phenotype," (b) repeating (a) for each of the multiple levels of stimulus to thereby produce a separate quantitative phenotype of the cells at each level of stimulus; and (c) identifying a path through the separate quantitative phenotypes of cells exposed to the stimulus. The stimulus can take many different forms. Examples include exposure to chemical compounds, exposure to biological agents, exposure to electromagnetic radiation, exposure to particle radiation, exposure to an electrical or magnetic field or force, exposure to a mechanical field or force, and combinations of these. In some cases, the multiple levels of stimulus are multiple durations of after an initial exposure to the stimulus. In this embodiment, the cells are analyzed at various times after exposure.

In particularly preferred embodiments, at least some feature values comprising the quantitative phenotypes are obtained from an image of the cells. These feature values may characterize cell morphology, statistical features of cells (sometimes derived from intensity histograms), biological classification of the cells, and the like. In one example, a biological classification specifies a cell cycle state.

Sometimes a graphical representation of the path provides the most useful information. In a particularly preferred embodiment, the graphical representation is provided along one or more principle components obtained via a principle component analysis.

Another aspect of the invention pertains to apparatus for analyzing images of cells exposed to multiples of a stimulus and generating a response path based on those images. The apparatus includes at least (a) an interface configured to receive the images of the cells that have been exposed to said multiple levels of a stimulus; (b) a memory for storing, at least temporarily, some or all of the images; and (c) one or more processors in communication with the memory and designed or configured to generate the response path by a technique of the type described herein. Typically, the apparatus will also include a display that is capable of graphically depicting the response path.

As indicated, the invention provides particular value when used to determine whether a first compound and a second compound act on cells by a related mechanism of action. Thus, another aspect of the invention may be characterized by the following sequence: (a) for each of multiple concentrations of the first compound, obtaining a plurality of feature values characterizing the phenotype of cells exposed to the particular concentration of the first compound, to thereby produce a plurality of first concentration-specific phenotypes; (b) identifying a first path through the first concentration-specific phenotypes of cells exposed to the first compound; (c) for each of multiple concentrations of the second compound, obtaining a plurality of feature values characterizing the phenotype of cells exposed to the particular concentration of the second compound, to thereby produce a plurality of second concentration-specific phenotypes; (d) identifying a second path through second concentration-specific phenotypes of cells exposed to the second compound; and (e) comparing the first and second paths, wherein a degree of similarity between the paths corresponds to a degree of similarity in the mechanism of action of the first and second compounds. In some particularly valuable applications, at least one of the first and second compounds is a known therapeutic or potential therapeutic.

The concentrations of the compounds should vary over an active range. The multiple concentrations of the first compound typically vary from lowest to highest by a factor of at least about two. Preferably, the multiple concentrations of the first compound include at least five separate concentrations of the first compound, and more preferably at least eight separate concentrations of the first compound.

As mentioned above in the context of the first aspect of the invention, the feature values may be provided from a number of different sources. Particularly valuable phenotypic features are provided by image analysis and associated processes. In a particularly preferred embodiment of this aspect of the invention, the feature values include numeric values characterizing one or more of the following cellular components: DNA, Golgi, cytoskeletal components such as tubulin and actin, and the plasma membrane. In a specific embodiment, the plurality of feature values include numeric values characterizing one or more of the following cellular components: DNA, Golgi, and tubulin.

In one approach, the comparison simply involves graphically depicting the first and second paths together. Preferably, the graphical depiction presents the first and second paths in a space defined by principal components. Thus, in some embodiments, the method also involves using the concentration specific phenotypes in a technique that provides a reduced-dimensionality space in which to depict the paths (e.g., principal component analysis, linear and non-linear discriminant analysis, multidimensional scaling, and projection pursuit techniques).

Another aspect of the invention pertains to computer program products including machine-readable media on which are stored program instructions for implementing at least some portion of the methods described above. Any of the methods of this invention may be represented, in whole or in part, as program instructions that can be provided on such computer readable media. In addition, the invention pertains to various combinations of data and data structures generated and/or used as described herein.

These and other features and advantages of the present invention will be described in more detail below with reference to the associated figures.

BRIEF DESCRIPTION OF THE DRAWINGS

The patent or application file contains at least one drawings executed in color. Copies of this patent or patent application publication with color drawing(s) will be provided by the Office upon request and payment of the necessary fee.

DETAILED DESCRIPTION OF THE PREFERRED EMBODIMENTS

Figure 1:
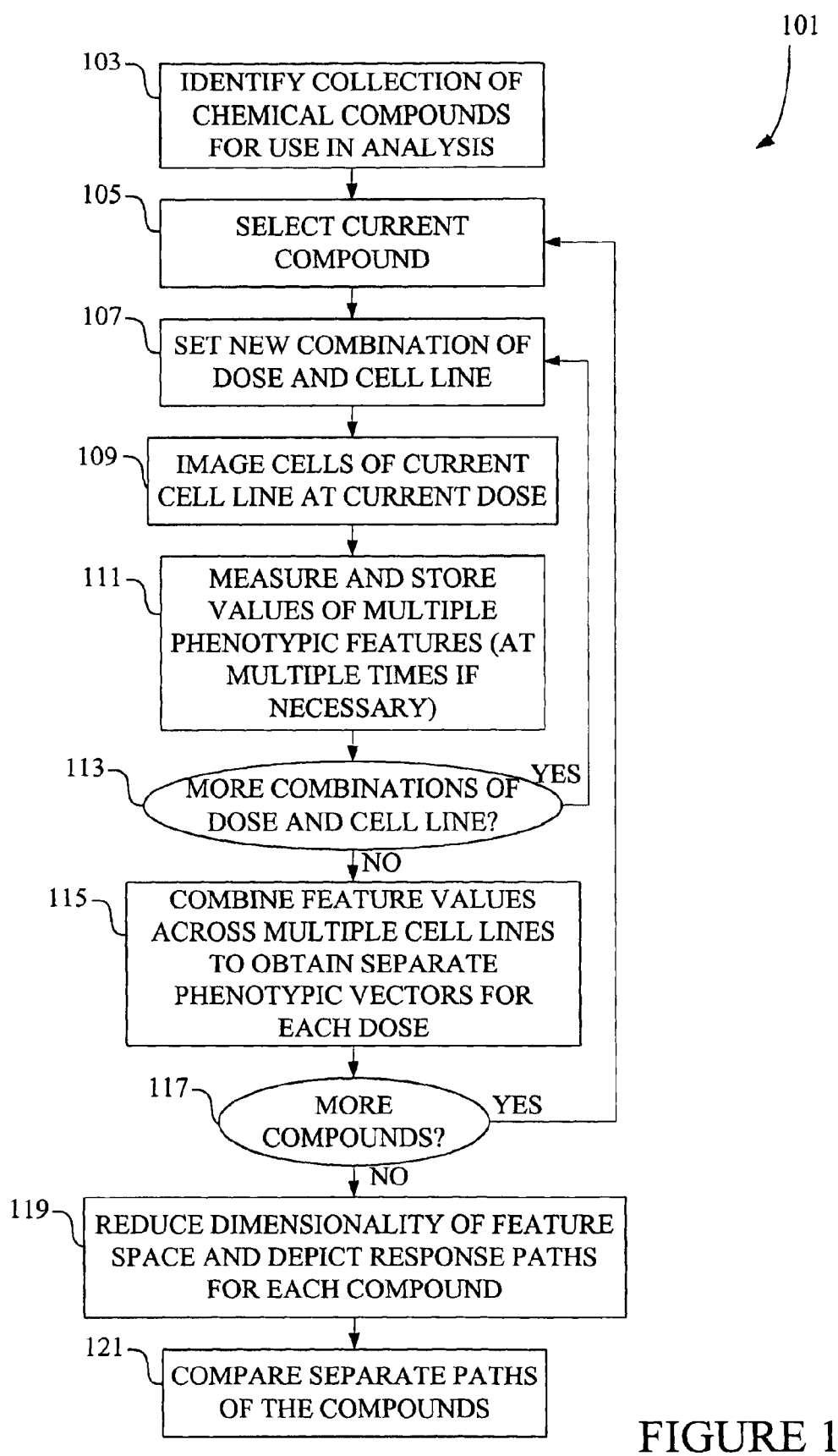
FIG. 1 is a process flow chart depicting the preparation and use of a stimulus response curve based upon phenotypic data.

The present invention allows for comparison and visualizing of response curves in multidimensional space. The response curves may span various levels of a stimulus, with each point in the curve representing a different level of the stimulus. For example, each point might represent a different concentration or dose of chemical compound. Alternatively, each point in the curve may represent a different time after initial exposure to a chemical compound. Importantly, each point in the response curve contains multivariate information about a cell's or population of cells' response to a particular level of the stimulus. Preferably, this multivariate information contains some phenotypic information about the cell. Such phenotypic information may provide morphological details, statistical details, and/or higher level biological characterizations of the cell or cell population. In an especially preferred embodiment, such features are extracted directly or indirectly from images of the cells. Of course, the multivariate information in the data points may include non-phenotypic information as well. Such information can derive from any of a number of different tests and/or other sources such as public literature and databases.

One important advantage of the present invention is that it allows related stimuli to be compared in a manner that accounts for complicated interactions between multiple phenotypic variables. Such comparisons help identify trends and allow characterization of particular stimuli. The comparisons may be accomplished by a computing device and/or human observers. To the extent that human observers are involved in the comparison, it will be beneficial to depict the multivariate response curves in a space that emphasizes variations in the data. For example, the invention may involve depicting the response paths in a space defined by principle components. In this manner, complicated multivariate data is depicted so that it can be easily comprehended. To the extent that a quantitative comparison is required, a computing device may compare two or more response curves by any of a number or techniques. Such techniques include distance techniques, clustering techniques and the like.

Process Overview and Relevant Definitions

Some of terms used herein are not commonly used in the art. Other terms may have multiple meanings in the art. Therefore, the following definitions are provided as an aid to understanding the description that follows. The invention as set forth in the claims should not necessarily be limited by these definitions.

The term "component" or "component of a cell" refers to a part of a cell having some interesting property that can be employed to derive biologically relevant information using image analysis. General examples of cell components include biomolecules and cellular organelles. Specific examples of biomolecules that could serve as cell components for use with this invention include proteins, lipids, polysaccharides, proteins, etc. Sometimes, the relevant component will refer to a group of structurally or functionally related biomolecules. Alternatively, the component may represent a portion of a biomolecule such as a polysaccharide group on a protein, or a particular sequence of a nucleic acid or protein. Collections of molecules such as micells can also serve as cellular components for use with this invention. And subcellular structures such as vesicles and organelles may also serve the purpose.

The term "marker" or "labeling agent" refers to materials that specifically bind to and label cell components. These markers or labeling agents should be detectable in an image of the relevant cells. Typically, a labeling agent emits a signal whose intensity is related to the concentration of the cell component to which the agent binds. Preferably, the signal intensity is directly proportional to the concentration of the underlying cell component. The location of the signal source (i.e., the position of the marker) should be detectable in an image of the relevant cells.

Preferably, the chosen marker binds indiscriminately with its corresponding cellular component, regardless of location within the cell. Although in other embodiments, the chosen marker may bind to specific subsets of the component of interest (e.g., it binds only to sequences of DNA or regions of a chromosome). The marker should provide a strong contrast to other features in a given image. To this end, the marker should be luminescent, radioactive, fluorescent, etc. Various stains and compounds may serve this purpose. Examples of such compounds include fluorescently labeled antibodies to the cellular component of interest, fluorescent intercalators, and fluorescent lectins. The antibodies may be fluorescently labeled either directly or indirectly.

The term "stimulus" refers to something that may influence the biological condition of a cell. Often the term will be synonymous with "agent" or "manipulation." Stimuli may be materials, radiation (including all manner of electromagnetic and particle radiation), forces (including mechanical (e.g., gravitational), electrical, magnetic, and nuclear), fields, thermal energy, and the like. General examples of materials that may be used as stimuli include organic and inorganic chemical compounds, biological materials such as nucleic acids, carbohydrates, proteins and peptides, lipids, various infectious agents, mixtures of the foregoing, and the like. Other general examples of stimuli include non-ambient temperature, non-ambient pressure, acoustic energy, electromagnetic radiation of all frequencies, the lack of a particular material (e.g., the lack of oxygen as in ischemia), temporal factors, etc.

Specific examples of biological stimuli include exposure to hormones, growth factors, antibodies, or extracellular matrix components. Or exposure to biologics such as infective materials such as viruses that may be naturally occurring viruses or viruses engineered to express exogenous genes at various levels. Biological stimuli could also include delivery of antisense polynucleotides by means such as gene transfection. Stimuli also could include exposure of cells to conditions that promote cell fusion. Specific physical stimuli could include exposing cells to shear stress under different rates of fluid flow, exposure of cells to different temperatures, exposure of cells to vacuum or positive pressure, or exposure of cells to sonication. Another stimulus includes applying centrifugal force. Still other specific stimuli include changes in gravitational force, including sub-gravitation, application of a constant or pulsed electrical current. Still other stimuli include photobleaching, which in some embodiments may include prior addition of a substance that would specifically mark areas to be photobleached by subsequent light exposure. In addition, these types of stimuli may be varied as to time of exposure, or cells could be subjected to multiple stimuli in various combinations and orders of addition. Of course, the type of manipulation used depends upon the application.

The term "phenotype" generally refers to the total appearance of an organism or cell from an organism. In the context of this invention, cellular phenotypes and their representations in processing systems (e.g., computers) are particularly interesting. A given cell's phenotype is a function of its genetic constitution and environment. Often a particular phenotype can be correlated or associated with a particular biological condition or mechanism of action resulting from exposure to a stimulus. Generally, cells undergoing a change in biological conditions will undergo a corresponding change in phenotype. Thus, cellular phenotypic data and characterizations may be exploited to deduce mechanisms of action and other aspects of cellular responses to various stimuli.

A selected collection of data and characterizations that represent a phenotype of a given cell or group of cells is sometimes referred to as a "quantitative cellular phenotype." This combination is also sometimes referred to as a phenotypic fingerprint or just "fingerprint." The multiple cellular attributes or features of the quantitative phenotype can be collectively stored and/or indexed, numerically or otherwise. The attributes are typically quantified in the context of specific cellular components or markers. Measured attributes useful for characterizing an associated phenotype include morphological descriptors (e.g., size, shape, and/or location of the organelle) and composition (e.g., concentration distribution of particular biomolecules within the organelle). Other attributes include changes in a migration pattern, a growth rate, cord formation, an extracellular matrix deposition, and even cell count.

The quantitative phenotypes may themselves serve as individual points on response curves of this invention. A phenotypic response to stimulus may be characterized by exposing various cell lines to a stimulus of interest at various levels (e.g., doses of radiation or concentrations of a compound). In each level within this range, the phenotypic descriptors of interest are measured to generate quantitative phenotypes associated with levels of stimulus.

The term "path" or "response curve" refers to the characterization of a stimulus at various levels. For example, the path may characterize the effect of a chemical applied at various concentrations or the effect of electromagnetic radiation provided to cells at various levels of intensity or the effect of depriving a cell of various levels of a nutrient. Mathematically, the path is made up of multiple points, each at a different level of the stimulus. In accordance with this invention, each of these points is preferably a collection of parameters or characterizations describing some aspect of a cell or collection of cells. Typically, at least some of these parameters and/or characterizations are derived from images of the cells. In this regard, they represent quantitative phenotypes of the cells. In the sense that each point in the path may contain more than one piece of information about a cell, the points may be viewed as arrays, vectors, matrices, etc. To the extent that the path connects points containing phenotypic information (separate quantitative phenotypes), the path itself may be viewed as a "concentration-independent phenotype."

As used herein, the term "feature" refers to a phenotypic property of a cell or population of cells. Typically, the points in a response curve of this invention are each comprised of multiple features. The terms "descriptor" and "attribute" may be used synonymously with "feature." Features derived from cell images include both the basic "parameters" extracted from a cell image and the "biological characterizations" (including biological classifications such as cell cycle states). The latter example of a feature is typically obtained from an algorithm that acts on the basic parameters. The basic parameters are typically morphological, concentration, and/or statistical values obtained by analyzing a cell image showing the positions and concentrations of one or more markers bound within the cells.

FIG. 1 depicts a sample process flow for generating and using response paths in accordance with an embodiment of this invention. As depicted in FIG. 1, a process 101 begins by identifying a collection of chemical compounds for use in the analysis. See block 103. This operation may be performed by a computing apparatus or possibly by one or more human beings. The compounds selected at 103 will ultimately be used to generate data that defines a "phenotypic space" for comparing multiple response paths.

After the relevant collection of chemical compounds has been identified at 103, the process next selects one current compound at 105. Each compound represents a cycle in an iterative process in which multiple compounds are analyzed to generate relevant phenotypic data. Each new iteration begins with operation 105. In practice, multiple compounds may be analyzed in parallel, so the iterative/sequential nature of the process may not be strictly accurate. Regardless of how the process is depicted, multiple compounds are evaluated at some point. The flow chart simply depicts this fact.

With a current compound selected, the process next selects a particular combination of compound dose and cell line for application of the dose. See block 107. In a preferred embodiment, each compound has an associated matrix of cell lines and doses. This matrix represents the fact that multiple distinct cell lines are treated with the compound of interest, each at multiple doses. Each combination of dose and cell line provides separate phenotypic information. Ultimately, the response curve passes through distinct points, each representing a separate dose. At each dose, the phenotypic information spans multiple cell lines. In principle, the points on the response path can be confined to a single cell line.

After the current combination of dose and cell line has been selected and provided, the process next images the cells of the current cell line that have been exposed to the current compound at the current dose. See block 109. If more than one cell component is to be considered, the imaging apparatus may generate multiple images, one for each cell component/marker combination. At 111, the process performs an image analysis that measures and stores parameter values. In some embodiments, these features will be separately extracted from multiple images of the cell line taken at different times after exposure to the compound. At 113, the process determines whether there are additional combinations of dose and cell lines to be considered. If so, process control returns to 107 where the next combination of dose and cell line is selected.

Ultimately, all the relevant combinations of dose and cell line for a given compound have been imaged and analyzed. At that point, process control proceeds to block 115 where the system combines feature values across multiple cell lines to obtain separate phenotypic vectors for each separate dose. These phenotypic vectors represent the individual points in a response path associated with the current compound.

At 117, the process determines whether there are more compounds to be considered as part of the analysis. If so, process control returns to block 105 where the next current compound is selected. Thereafter, that compound is treated as described above with respect to blocks 107 through 115.

Note that some or all of the operations described above for each compound may be automated and performed by a machine. The machine operations may be performed by various image acquisition and image analysis apparatus.

After each of the compounds from the collection identified at 103 have been analyzed as described above, the process has numerous phenotypic vectors (quantitative phenotypes), each of which is associated with a particular combination of chemical compound and dose. Each of the vectors represents a point in multidimensional space. The numerous dimensions may be difficult to depict in a manner that presents meaningful information to a human viewer. Therefore, process 101 next reduces the dimensionality of feature space and depicts response paths for each compound in the reduced dimensional space. See 119. One preferred approach to this involves performing a principle component analysis on the collection of separate phenotypic vectors. After the reduced dimensional space has been generated, the system may next compare the separate paths of the individual compounds. See 121. This can provide relevant information about the mechanism of action of the various compounds. It allows a human or computer algorithm to compare the various paths and draw conclusions about the mechanisms of action of the various compounds. Note that it is not strictly necessary to depict the response paths in a reduced dimensional space prior to comparing the separate paths. Thus, if a computing device is used to do the comparison, then operation 119 may be optional.

Note that the discussion of process 101 treats exposure to chemical compounds as the stimuli of interest. The process 101 can be extended to cover any particular stimulus, not just exposure to chemical compounds. As mentioned, stimuli of interest to the present invention include exposure to biological agents, exposure to various fields, forces, and radiation, deprivation of agents important for normal cell growth and functioning, etc.

Also, alternative definitions of response path that do not involve variation over dose or time could be employed. For example, a path could be provided through multiple distinct cell lines, where each point on the path represents a different cell line.

Selecting Experiments for Providing Response Paths

Initially, a relevant collection of stimuli for consideration in the analysis must be selected. As mentioned, the stimuli suitable for use with this invention span a wide range of physical agents, forces, fields, etc. Generally, the collection of stimuli chosen for a particular analysis may be selected with no prior assumptions. More often, the stimuli are selected because they are believed to have related and interesting effects on cells. In the case of potential therapeutic compounds, a number of chemical compounds may be selected because they are believed to have a similar mechanism of action when applied to particular cells. For example, compounds may be selected because they are believed to possess anti-mitotic properties when applied to cancer cells.

The data used for the analysis of the invention may be derived from a wide range of experiments. Such experiments typically span a matrix of experimental conditions. Such matrix may include experimental variations in the choice of stimulus, the level of each stimulus, the cell lines to which the stimulus is applied, and the particular components within a cell line that are analyzed. Multiple compounds may be applied in multiple concentrations to multiple cell lines. For each combination of compound, dose, and cell line, multiple images may be obtained. Each such image contains information about a separate component/marker combination within the cell. Note that the invention is not limited to this wide-ranging matrix. At its essence, the invention simply involves considering a single stimulus at multiple levels. Of course, each such level should provide multivariate data about a cell phenotype. However, it is unnecessary to employ multiple cell lines and/or multiple cellular components in generating the relevant multivariate data.

The component/marker combinations used in a particular study should be chosen based upon the area of interest. For example, oncology investigations may require a different set of markers than cardiovascular investigations. Further, the choice of markers should vary over a range of cell biology. For example, it typically would be unnecessary to choose two separate markers that both image microtubules. Depending upon the application, the markers can have a very high degree of specificity, as in the case of an antibody for tubulin or can be more lower degree of specificity, as in the case of lectins. Note that some lectins, such as Lens culinaris (LC) lectin actually binds to various polysaccharides. Because most of the time these polysaccharides components are enriched in the Golgi, LC lectin still can be an effective marker for Golgi.

Generally, cell components tracked in presently preferable embodiments can include proteins, protein modifications, genetically manipulated proteins, exogenous proteins, enzymatic activities, nucleic acids, lipids, carbohydrates, organic and inorganic ion concentrations, sub-cellular structures, organelles, plasma membrane, adhesion complex, ion channels, ion pumps, integral membrane proteins, cell surface receptors, G-protein coupled receptors, tyrosine kinase receptors, nuclear membrane receptors, ECM binding complexes, endocytotic machinery, exocytotic machinery, lysosomes, peroxisomes, vacuoles, mitochondria, Golgi apparatus, cytoskeletal filament network, endoplasmic reticulum, nuclear membrane, proteosome apparatus, chromatin, nucleolus, cytoplasm, cytoplasmic signaling apparatus, microbe specializations and plant specializations.

The following table illustrates some cell components and markers (labeling agents) that may be used in embodiments of the present invention. Other markers can be used in various embodiments without departing from the scope of the invention.

| Cell component | Marker or Component | Disease State |
|---|---|---|
| Plasma membrane (including overall cell shape) | Carbocyanine dyes Phosphatidylserine Various lipids Glycoproteins | Apoptosis-Cancer Apoptosis-Neural degenerative Ds |
| Adhesion complexes | Cadherins Integrins Occludin Gap junction ERM proteins CAMs Catenins Desmosomes | Thrombosis Metastasis Wound healing Inflammatory Ds Dermatologic Ds |
| Ion Channels and Pumps | Na/K Atpase Calcium channels Serotonin reuptake pump CFTR SERCA | Cystic fibrosis Depression Congestive Heart Failure Epilepsy |
| G coupled receptors | β adrenergic receptor Angiotensin receptor | Hypertension Heart Failure Angina |
| Tyrosine kinase receptors | PDGF receptor FGF receptor IGF receptor | Cancer Wound healing Angiogenesis Cerebrovascular Ds |
| ECM binding complexes | Dystroglycan Syndecan | Muscular Dystrophy |
| Endocytotic machinery | Clathrin Adaptor proteins COPs Presenilins Dynamin | Alzheimer's Ds |
| Exocytotic machinery | SNAREs Vesicles | Epilepsy Tetanus Systemic Inflammation Allergic Reactions |
| Lysosomes | Acid phosphatase Transferrin Lysotracker Red | Viral diseases |
| Peroxisomes/Vacuoles | | Neural degenerative Ds |
| Mitochondria | Caspases Apoptosis inducing factor F1 ATPase Fluorescein Cyclo-oxygenase Mitotracker Red Mitotracker Green | Apoptosis Neural degenerative Ds Mitochondrial Cytopathies Inflammatory Ds Metabolic Ds |
| Golgi Apparatus | Lens culinaris lectin DiOC6 carbocyanine dye COPs Antibodies specific for Golgi | |
| Cytoskeletal Filament Networks | Microtubules Actin Intermediate Filaments Kinesin, dynein, myosin Microtubule associated proteins Actin binding proteins Rac/Rho Keratins GFAP Von Wiltbrand's factor | Cancer Neural degenerative Ds Inflammatory Ds Cardiovascular Ds Skin Ds |
| Endoplasmic Reticulum | SNARE PDI Ribosomes | Neural degenerative Ds |
| Nuclear Membrane | Lamins Nuclear Pore Complex | Cancer |
| Proteosome Apparatus | Ubiquityl transferases | Cancer |
| Chromatin | DNA Histone proteins Histone deacetylases Telomerases | Cancer Aging |
| Nucleolus | Phase markers | |
| Cytoplasm | Intermediary Metabolic Enzymes BRCA1 | Cancer |
| Cytoplasmic Signaling Apparatus | Calcium Camp PKC pH | Cardiovascular Ds Migraine Apoptosis Cancer |
| Microbe Specializations | Flagella Cilia Cell Wall components: Chitin synthase | Infectious Ds |
| Plant specializations | Choloroplast Cell Wall components | Crop Protection |

In one preferred embodiment, the cellular components considered in separate images include one ore more of DNA, cytoskeletal proteins, and Golgi. In a specific embodiment, the images for each combination of cell line, dose, and compound include a DNA image, a tubulin image, and a Golgi image. Various markers can be used for each of these components. In a preferred embodiment, the DNA marker is DAPI, the tubulin marker is an antibody specific for tubulin, and the Golgi marker is LC lectin.

In one specific approach, the above three markers are analyzed using two separate processes. In a first process, a cell line is simply stained with a marker for DNA. In a second run, the cell line is stained with all three markers. The first process run is used to simply identify cell cycle information. For example, this run is used to determine the proportion of cells in each separate phase of the cell cycle (G1, S, G2, M, and/or various subphases of M). The two process runs are employed because imaging tubulin and Golgi require repeating washing of the cells. This process selectively causes some cells to wash away; specifically rounded up and mitotic cells. Therefore, the remaining cells imaged for tubulin and Golgi are biased toward interphase states.

Regarding the doses or "levels" of the various stimuli, one should endeavor to choose a range of doses that define and active zone for affecting phenotype in a cell line of interest. In one approach, researchers perform a preliminary experiment with each drug. The preliminary experiment may involve titration across a wide range of concentrations. The titration may measure cell count or other appropriate biological parameter. An upper boundary of the active zone may be a concentration at which further increases of concentration have no additional affect on the cells. For example, the upper boundary may be the minimum concentration at which all cells are killed. A lower bound of the active zone is the lowest concentration at which some biological affect can be observed.

In some cases, the highest dose allowed by the process is governed by some physical parameter such as the maximum solubility of a compound. Alternatively, it may be governed by the maximum volume of a compound solution that can be administered to a well without having the solvent significantly affect the cells.

In a preferred embodiment, a highest level of the stimuli is first identified by some technique. Then, additional lower level of the stimulus are identified by incremental reductions. For example, in the case of a chemical compound, serial dilutions may be performed to generate lower level doses. At a minimum, at least two levels of the stimulus must be considered. Preferably significantly more levels are considered. In a preferred embodiment, at least five separate stimulus levels are considered. In a specific preferred embodiment, eight separate levels are considered. If a chemical compound serves as the stimulus, then the highest concentration of the compound should be at least about two times that of the lowest concentration.

As indicated, phenotypic vectors for given stimuli and level combinations may include multivariate information taken from different cell lines. However, this need not be the case, as all the multivariate data of interest may be obtained from a single cell line. Generally, a researcher will chose one or a range of cell lines that are relevant to the area of interest. For example, if the researcher focuses on oncology applications, the cell lines chosen may include different types of cancers and possibly other cells lines that allow one to identify typical side effects of anti cancer drugs. In one specific embodiment pertaining to oncology, six different cell lines are considered. These include HUVEC (human umbilical vein endothelial cells), A498, A548, SF268, SKOV3, and DU145.

Imaging

As indicated, the phenotypic data characterizing each point on a response curve is derived, at least in part, from images of cell lines exposed to particular combinations of stimulus type and stimulus level. See block 109 in FIG. 1, for example. Various techniques for preparing and imaging appropriately treated cells are described in U.S. patent application Ser. Nos. 09/310,879, 09/311,996, and 09/311,890, previously incorporated by reference. In the case of cells treated with a fluorescent marker, a collection of such cells is illuminated with light at an excitation frequency. A detector is tuned to collect light at an emission frequency. The collected light is used to generate an image, which highlights regions of high marker concentration.

Additional operations may be performed prior to, during, or after the imaging operation (109) of FIG. 1. For example, "quality control algorithms" may be employed to discard image data based on, for example, poor exposure, focus failures, foreign objects, and other imaging failures. Generally, problem images can be identified by abnormal intensities and/or spatial statistics.

In a specific embodiment, a correction algorithm may be applied prior to segmentation to correct for changing light conditions, positions of wells, etc. In one example, a noise reduction technique such as median filtering is employed. Then a correction for spatial differences in intensity may be employed. In one example, the spatial correction comprises a separate model for each image (or group of images). These models may be generated by separately summing or averaging all pixel values in the x-direction for each value of y and then separately summing or averaging all pixel values in the y direction for each value of x. In this manner, a parabolic set of correction values is generated for the image or images under consideration. Applying the correction values to the image adjusts for optical system non-linearities, mis-positioning of wells during imaging, etc.

The production of the images includes cell plating, compound dilution, compound addition and imaging focusing. Failures in any these systems can be detected by a variety of methods. For example, cell plating could fail because of a clogged tip in a delivery pipette. Such failure can be identified by adding a fluorescent dye or bead to the cell suspension. The fluorescence of this dye or bead is chosen to be at a different channel (wavelength) than the markers used to image cellular components. Another potential failure could occur during compound delivery. To detect such failures, one can add a fluorescent dye or bead in the compound plate before compound dilution. The amount of fluorescent dye or bead is proportional to the amount of compound. Yet another potential problem occurs when the focus of the image acquisition system changes during imaging. To account for such spatial biases, one can employ control wells containing, for example, cells with no or neutral compounds interspersed throughout the plate. Still another problem results from foreign objects (e.g., small dust particles) in the well. This can be addressed with image segmentation and statistical outlier identification techniques.

Generally the images used as the starting point for the methods of this invention are obtained from cells that have been specially treated and/or imaged under conditions that contrast the cell's marked components from other cellular components and the background of the image. Typically, the cells are fixed and then treated with a material that binds to the components of interest and shows up in an image (i.e., the marker). Preferably, the chosen agent specifically binds to DNA, but not to most other cellular biomolecules.

Multivariate Phenotypic Data from Images

At every combination of dose, cell line, and compound, one or more images are obtained. As mentioned, these images are used to extract various parameter values of relevance to a biological, phenotypic characterization of the compound of interest. Generally a given image of a cell, as represented by one or more markers, can be analyzed to obtain any number of image parameters. These parameters are typically statistical or morphological in nature. The statistical parameters typically pertain to a concentration or intensity distribution or histogram. The parameters chosen for use with this invention should relate to the expected biological response of the cell lines to the compound of interest. The parameters should also represent a diverse set of phenotypic characteristics.

Some general parameter types suitable for use with this invention include a cell count, an area, a perimeter, a length, a breadth, a fiber length, a fiber breadth, a shape factor, a elliptical form factor, an inner radius, an outer radius, a mean radius, an equivalent radius, an equivalent sphere volume, an equivalent prolate volume, an equivalent oblate volume, an equivalent sphere surface area, an average intensity, a total intensity, an optical density, a radial dispersion, and a texture difference. These parameters can be average or standard deviation values, or frequency statistics from the descriptors collected across a population of cells. In some embodiments, the parameters include features from different cell portions or cell types.

Examples of some specific parameters/descriptors that may be suitable for use in multivariate response paths of this invention are included in the following table. Other descriptors can also be used without departing from the scope of the invention.

| Name of Parameter | Explanation/Comments |
| --- | --- |
| Count | Number of objects |
| Area | |
| Perimeter | |
| Length | X axis |
| Width | Y axis |
| Shape Factor | Measure of roundness of an object |
| Height | Z axis |
| Radius | |
| Distribution of Brightness | |

-continued

| Name of Parameter | Explanation/Comments |
|---|---|
| Radius of Dispersion | Measure of how dispersed the marker is from its centroid |
| Centroid location | x–y position of center of mass |
| Number of holes in closed objects | Derivatives of this measurement might include, for example, Euler number (= number of objects − number of holes) |
| Elliptical Fourier Analysis (EFA) | Multiple frequencies that describe the shape of a closed object |
| Wavelet Analysis | As in EFA, but using wavelet transform |
| Interobject Orientation | Polar Coordinate analysis of relative location |
| Distribution Interobject Distances | Including statistical characteristics |
| Spectral Output | Measures the wavelength spectrum of the reporter dye. Includes FRET |
| Optical density | Absorbance of light |
| Phase density | Phase shifting of light |
| Reflection interference | Measure of the distance of the cell membrane from the surface of the substrate |
| 1, 2 and 3 dimensional Fourier Analysis | Spatial frequency analysis of non closed objects |
| 1, 2 and 3 dimensional Wavelet Analysis | Spatial frequency analysis of non closed objects |
| Eccentricity | The eccentricity of the ellipse that has the same second moments as the region. A measure of object elongation. |
| Long axis/Short Axis Length | Another measure of object elongation. |
| Convex perimeter | Perimeter of the smallest convex polygon surrounding an object |
| Convex area | Area of the smallest convex polygon surrounding an object |
| Solidity | Ratio of polygon bounding box area to object area. |
| Extent | proportion of pixels in the bounding box that are also in the region |
| Granularity | |
| Pattern matching | Significance of similarity to reference pattern |
| Volume measurements | As above, but adding a z axis |
| Number of Nodes | The number of nodes protruding from a closed object such as a cell; characterizes cell shape |
| End Points | Relative positions of nodes from above |

The features used in the actual points comprising a response path of this invention may be parameters directly extracted from the images or they may be biological characterizations derived from the parameters. Note that the points may also include some features that were not directly or indirectly obtained from the images. For example, the points may include information obtained from public sources such as databases, literature, etc. Further, the features comprising the points may include non-image related data, such as data obtained from chemical and biological assays.

Often, the parameters are chosen based upon a biological understanding. For example, if a cell's state in the cell cycle is important to the biological problem being investigated, then parameters that characterize the amount of DNA in a cell and/or the degree of condensation of that DNA into chromosomes is relevant. In a specific example, cell cycle parameters include the total quantity of DNA in a nucleus, the area of the nucleus, and the intensity variance of the cellular DNA. A full discussion of the relevant parameters for characterizing the cell cycle is presented in U.S. patent application Ser. No. 09/729,754, previously incorporated by reference.

Similarly, if an objective is to characterize the Golgi in a cell, this can be accomplished with parameters that define the location of the Golgi with respect to the nucleus, describe the texture of the Golgi and describe the local concentration of Golgi components. The full discussion of the parameters relevant in characterizing Golgi is presented in U.S. patent application Ser. No. 09/792,012, (Publication No. 20020141631) previously incorporated by reference. Of specific interest, the Golgi complex in a perinuclear region may be characterized using parameters such as the mean, standard deviation, and kurtosis of pixel intensity, and various eigenvalues obtained by singular value decomposition of a pixel intensity matrix for the Golgi marker. From these parameters, the Golgi complex of a given cell may be characterized as normal, diffused, dispersed, or dispersed and diffused.

Further, if the cell shape provides further relevant phenotypic data, then parameters can be chosen accordingly. In one embodiment, a tubulin or other cytoskeletal component is marked and imaged to provide parameters relevant to cell shape. Specific examples of such parameters include the number of nodes on a cell image, the distance between end point of those nodes, a coefficient of tubulin polymerization (e.g., average pixel intensity of object pixels in a tubulin channel), averaged across all cells in a population, and a coefficient of microtubule reorganization (e.g., standard deviation of wavelet coefficients), averaged across all cells in a population. A full discussion of parameters relevant to characterizing cell shape can be found in U.S. patent application Ser. No. 09/792,013 (Publication No. 20020154798) previously incorporated by reference.

While a fundamental biological understanding can often direct one to the appropriate choice of parameters for use in this invention, a systematic analysis of data can help identify parameters that might not be immediately apparent. Such analysis can be conducted in a manner that finds parameters that are best able to show subtle differences in the response path. By considering the effect of varying a single parameter at a time, one can quickly home in the most relevant parameters for developing response curves in accordance with this invention.

As applied to specific markers, one preferred collection of parameters includes (1) total number of cells in a population of interest, (2) number of cells relative to number of cells in one or more controls, (3) proportion of cells in each of the stages of cell cycle (G1, S, G2, pre-anaphase mitotic, post-anaphase mitotic), (4) area of cell nuclei, averaged for each of the stages of the cell cycle, (5) diameter of cell nuclei, averaged for each of the stages of cell cycle, (6) axes ratio (measure of elongation) of nuclei, averaged for each of the stages of cell cycle, (7) eccentricity of nuclei (another measure of elongation), averaged for each of the stages of cell cycle, (8) solidity of nuclei (measure of a shape), averaged for each of the stages of cell cycle, (9) total intensity of nuclei pixels (a measure of amount of DNA in a cell), averaged for each of the stages of cell cycle, (10) variance of pixel intensities in a nucleus, averaged for each of the stages of cell cycle, (11) proportion of cells with normal Golgi in a subpopulation of cells in each stage of the cell cycle, (12) proportion of cells with diffuse Golgi in a subpopulation of cells in each stage of the cell cycle, (13) proportion of cells with dispersed Golgi in a subpopulation of cells in each stage of the cell cycle, (14) proportion of cells with dispersed and diffused Golgi in a subpopulation of cells in each stage of the cell cycle, (15) coefficient of the Golgi dispersion (kurtosis of the Golgi marker in a region of the cell), (16) coefficient of tubulin polymerization (average pixel intensity of object pixels in a tubulin channel), averaged across all cells in a population, and (17) coefficient of microtubule reorganization (standard deviation of wavelet coefficients), averaged across all cells in a population.

In a more specific embodiment, the parameter set for each dose/compound point in a response path includes parameters derived from DNA markers, Golgi markers, and tubulin markers. It is been found that the following ten parameters provide particularly useful phenotypic results.

1. The size of the nuclei as derived from a DNA marker. This value is provided as the average area of the nuclei of all interphase cells in an image.
2. The average ellipsicity of nuclei of interphase cells.
3. The difference between the proportion of interphase cells in $G_1$ and the proportion of interphase cells in $G_2$.
4. The proportion of interphase cells in S.
5. The "mitotic index" which specifies the proportion of mitotic cells in the image.
6. The proportion of interphase cells having normal Golgi.
7. The proportion of interphase cells having diffuse Golgi.
8. The proportion of interphase cells having diffuse and disperse Golgi.
9. The mean pixel intensity obtained from marked tubulin. This value is obtained by determining an overall threshold for the image and considering only objects having intensities above that threshold. The mean value of intensity of all pixels over the threshold is used.
10. A second order wavelet obtained from all pixels over the threshold value in the tubulin image.

In a particularly preferred specific embodiment, the above ten parameters are obtained for each of multiple cell lines, such as the six cell lines defined above, and packaged in a vector. This vector then represents a single dose/compound point to be used in a response path for the compound of interest. Note that this vector spans multiple cell lines and multiple phenotypic features. To obtain these various features, three separate markers were considered. A DNA marker was used for the first five parameters. A Golgi marker was used for the next three parameters. Finally, a tubulin marker was used for the last two parameters.

Visualization and Comparison of Response Paths

Lists of stimuli and associated quantitative phenotypes may be stored as database records or other data structures that can be queried or otherwise accessed as part of an analysis procedure. The stimuli may also be associated with other relevant data such as clinical toxicity, cellular toxicity, hypersensitivity, mechanism of action, etc. (when available). The stored phenotypic data is used to generate and depict response paths.

Various techniques may be employed to visualize the response paths generated as described above. In order for a human observer to make meaningful comparisons, the space in which the response paths are presented should be comprehendible. Note that for complicated quantitative phenotypes representing individual points on the path, there may be very many separate variables (60 in the example above). In principle, each of these variables represents a separate dimension. So one may be confronted with a 60 dimensional space, for example. Obviously, it becomes difficult to visualize meaningful trends or clusters in high dimensional space. Consider the problem of trying to visualize a trend in phenotypes comprised of three cellular components (e.g. tubulin, DNA and Golgi), each of which has multiple relevant parameters (e.g. total quantity of DNA and variance in the concentration of DNA). Obviously, there are more than three relevant dimensions to be considered in analyzing such phenotypes.

One possible solution to the problem involves selecting two or three dimensions (features) that are expected to be most relevant to a particular response curve. Unfortunately, it becomes impossible to view other potentially meaningful phenotypic features on the same two or three-dimensional space.

Various techniques may be employed to address this problem. Such techniques create a lower dimensional space in which the individual dimensions capture two or more features of the data. Examples of such techniques include principle component analysis, linear and non-linear discriminant analysis, multidimensional scaling, and projection pursuit techniques. A particularly preferred approach involves the use of principle component analysis. Principle component analysis determines the vectors (dimensions) through which a data set shows the greatest variation in multidimensional space. The first principle component shows the direction of greatest variation in the data. The second principle component shows the direction of the second greatest variation in data and so on. One can select as many principle components as are suitable to depict one's data. Typically, the first one, two, or three principle components are selected for presenting data to human observers. Principal component analysis is described more fully in Jackson, J. E. (1991) A User Guide to Principal Components. New York: John Wiley and Sons; and Jolliffe, I. T. (1986) Principal Component Analysis. New York: Springer-Verlag, both of which are incorporated herein by reference for all purposes.

Various commercially available tools for performing principle component analysis are available. One suitable statistical computing package for performing PCA is available from Insightful Corporation (formerly MathSoft) of Seattle, Wash. Principal component analysis can be applied to quantitative phenotypic data sets in a straight-forward manner. However, it will generally be necessary to standardize phenotypic data sets before submitting them to principle component analysis. This is because the various scalars that comprise the individual features of a quantitative phenotype reside on vastly different scales. For example, the mitotic index will range from zero to one hundred percent, while the size of the nuclei, average ellipsicity of the nuclei, average pixel intensity of the tubulin marker, etc. each have very different scales and associated units. To bring these various features onto a comparable scale for meaningful PCA analysis, one may perform transformations to standardize the data. In one preferred embodiment, each of the dimensions is scaled by considering all the data along that dimension (e.g., all values of nucleus area), subtracting the mean of that data and dividing by the standard deviation. This effectively scales the data for standardization.

After PCA is performed by a suitable tool, the results should be presented graphically. Various graphical tools are suitable for this purpose. One is provided by S+ Corporation. Another particularly useful graphical depiction tool is Spotfire.net available from SpotFire, Inc. of Cambridge, Mass. Any of these tools will not only present the data in principle component space, but will also identify which variables (features) contribute the most to each of the principle components. Because the present invention is concerned primarily with paths, the graphical depiction will preferably show connections between individual points along the dose response path for each particular stimulus.

Meaningful comparison between related stimuli requires that one identify patterns or trends in various response curves. This may be accomplished with or without the aid of a visualization technique/tool of the type described above. If a human observer is to participate in the pattern recognition, then such a visualization tool will typically provide great assistance. However, if a machine is to do the comparison, the reduced dimensional visualization technique may be unnecessary. Examples of techniques that may be employed for such comparison include techniques that determine an average difference or distance between two potentially related stimulus response curves, clustering, and the like.

Various examples applying principle component analysis to complex multivariate quantitative phenotypes are presented below. In these examples, dose response curves through multivariate phenotypes clearly show trends and clustering based upon mechanism of action.

In comparing response paths of potentially related stimuli, one typically identifies similarities in the general pathways. These similarities often show up in the path trajectories, starting and ending points, etc. In comparing stimuli such as exposure to chemical compounds, note that most drugs have response paths that follow reasonably similar trajectories at relatively low concentrations, but then diverge as the concentration increases. In other words, the phenotypic manifestations of distinct mechanisms of action only appear most pronounced at high concentrations.

Software/Hardware

Generally, embodiments of the present invention employ various processes involving data stored in or transferred through one or more computer systems. Embodiments of the present invention also relate to an apparatus for performing these operations. This apparatus may be specially constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein, or it may be more convenient to construct a more specialized apparatus to perform the required method steps. A particular structure for a variety of these machines will appear from the description given below.

In addition, embodiments of the present invention relate to computer readable media or computer program products that include program instructions and/or data (including data structures) for performing various computer-implemented operations. Examples of computer-readable media include, but are not limited to, magnetic media such as hard disks, floppy disks, and magnetic tape; optical media such as CD-ROM disks; magneto-optical media; semiconductor memory devices, and hardware devices that are specially configured to store and perform program instructions, such as read-only memory devices (ROM) and random access memory (RAM). The data and program instructions of this invention may also be embodied on a carrier wave or other transport medium. Examples of program instructions include both machine code, such as produced by a compiler, and files containing higher level code that may be executed by the computer using an interpreter.

Figure 2:
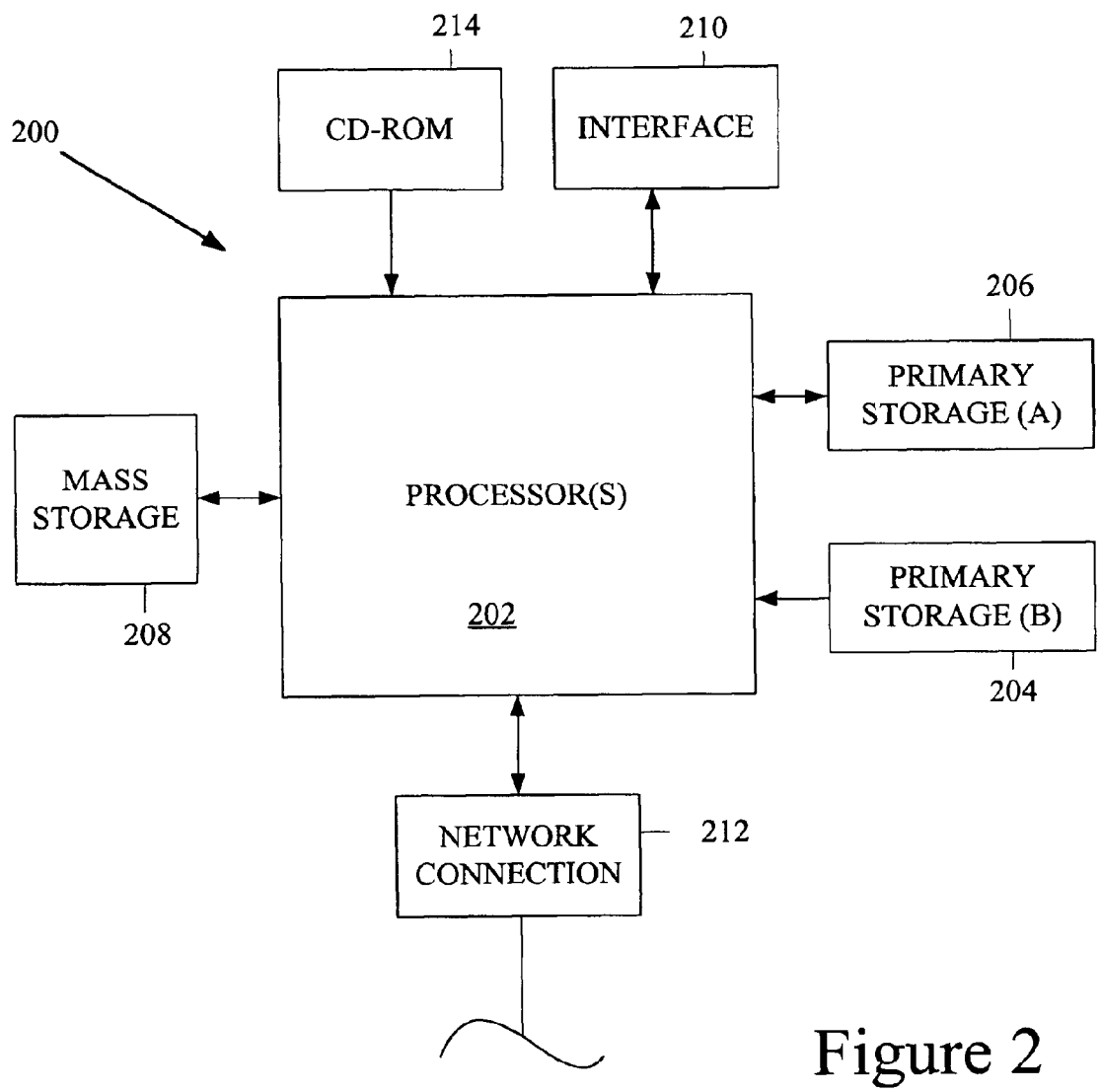
FIG. 2 is a simplified block diagram of a computer system that may be used to implement various aspects of this invention such as the various image analysis algorithms of this invention.

FIG. 2 illustrates a typical computer system that, when appropriately configured or designed, can serve as an image analysis apparatus of this invention. The computer system 200 includes any number of processors 202 (also referred to as central processing units, or CPUs) that are coupled to storage devices including primary storage 206 (typically a random access memory, or RAM), primary storage 204 (typically a read only memory, or ROM). CPU 202 may be of various types including microcontrollers and microprocessors such as programmable devices (e.g., CPLDs and FPGAs) and unprogrammable devices such as gate array ASICs or general purpose microprocessors. As is well known in the art, primary storage 204 acts to transfer data and instructions uni-directionally to the CPU and primary storage 206 is used typically to transfer data and instructions in a bi-directional manner. Both of these primary storage devices may include any suitable computer-readable media such as those described above. A mass storage device 208 is also coupled bi-directionally to CPU 202 and provides additional data storage capacity and may include any of the computer-readable media described above. Mass storage device 208 may be used to store programs, data and the like and is typically a secondary storage medium such as a hard disk. It will be appreciated that the information retained within the mass storage device 208, may, in appropriate cases, be incorporated in standard fashion as part of primary storage 206 as virtual memory. A specific mass storage device such as a CD-ROM 214 may also pass data uni-directionally to the CPU.

CPU 202 is also coupled to an interface 210 that connects to one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 202 optionally may be coupled to an external device such as a database or a computer or telecommunications network using an external connection as shown generally at 212. With such a connection, it is contemplated that the CPU might receive information from the network, or might output information to the network in the course of performing the method steps described herein.

In one embodiment, the computer system 200 is directly coupled to an image acquisition system such as an optical imaging system that captures images of cells. Digital images from the image generating system are provided via interface 212 for image analysis by system 200. Alternatively, the images processed by system 200 are provided from an image storage source such as a database or other repository of cell images. Again, the images are provided via interface 212. Once in the image analysis apparatus 200, a memory device such as primary storage 206 or mass storage 208 buffers or stores, at least temporarily, digital images of the cells. In addition, the memory device may store the quantitative phenotypes that represent the points on the response path. The memory may also store various routines and/or programs for analyzing the presenting the data, including the response paths. Such programs/routines may include programs for performing principal component analysis, regression analyses, path comparisons, and for graphically presenting the response paths.

EXAMPLES

As indicated above, an underlying premise of this invention is that changes in cell physiology are detectable through single-cell image analysis of cellular markers and, by measuring such changes in a sophisticated fashion, one can monitor biological similarities and differences between compounds. To characterize and demonstrate the ability of multivariate quantitative phenotype response paths to distinguish different classes of molecules, a panel of commercially available compounds with broad mechanisms of action was tested using the present invention. The types of compounds tested are listed in the following table.

| Class | Primary Protein Target | Number of Compounds |
|---|---|---|
| Calcium | Endoplasmic reticulum Ca2+ – ATPase | 3 |
| Calcium | Calmodulin | 6 |
| Cytoskeleton | Actin | 8 |
| Cytoskeleton | Tubulin | 9 |
| G Protein Effectors | G-proteins $G_i$ and $G_o$ | 4 |
| Gene Regulation | Topoisomerase II | 6 |
| Ion Pump | V-ATPase | 2 |
| Oxidative Phosphorylation | Mitochondrial ATPases | 3 |

-continued

| Class | Primary Protein Target | Number of Compounds |
| --- | --- | --- |
| Posttranslational Modification | Farnesyltransferase | 2 |
| Posttranslational Modification | Geranylgeranyltransferase 1 | 3 |
| Protein Kinase | p38 MAP kinase | 3 |
| Protein Kinase | PKC | 3 |
| Protein Kinase | p34cdc2/cyclin B | 4 |

Figure 3A:
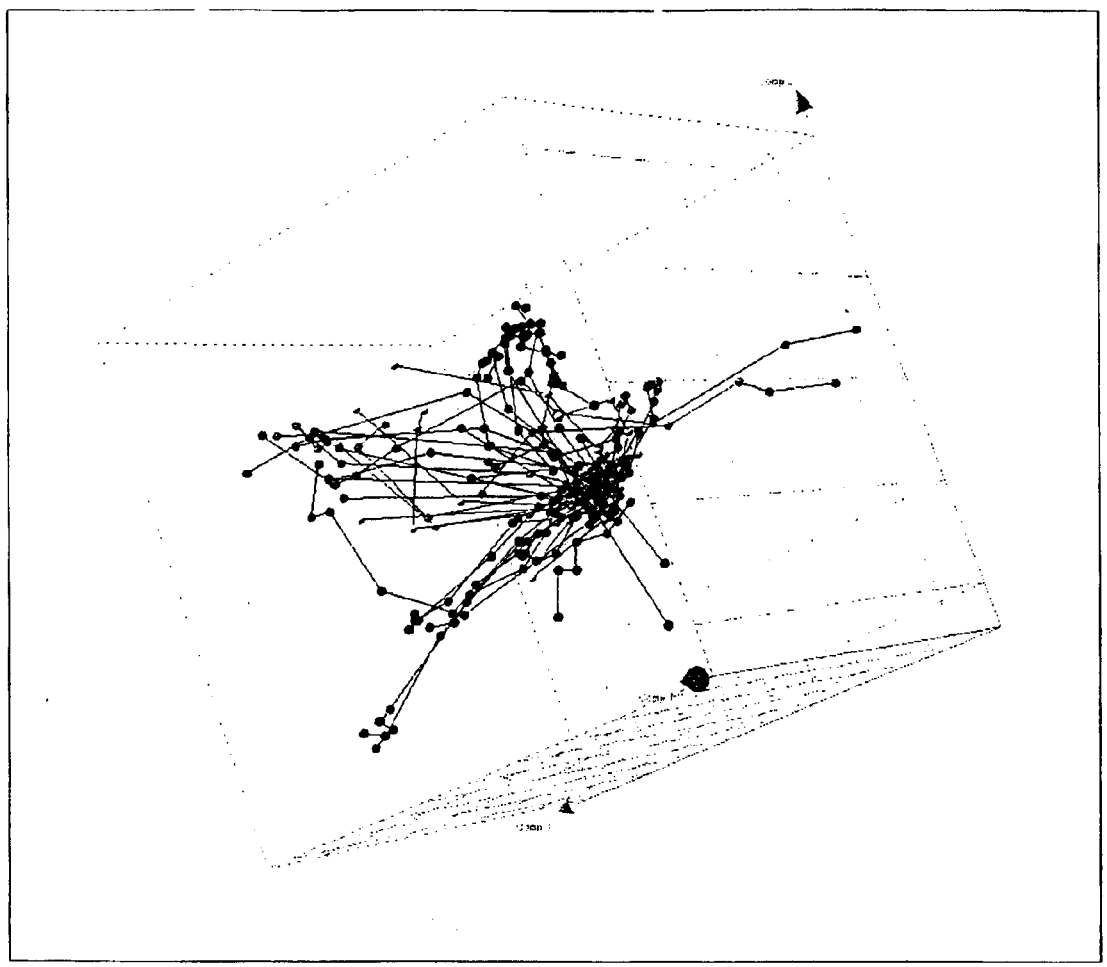
FIG. 3A is a plot of several dose response curves for compounds having known effects on targets; the curves are presented in a space defined by three principal components defined for multivariate phenotypic information.

A three-dimensional representation of three principal components calculated for each compound is shown in FIG. 3A. The data points are presented within the first three principal components obtained for the entire data set. Note that the controls cluster tightly in the center of the graph. The specific features and cell lines used to construct the quantitative phenotypes shown as points in the plot are set forth above in the "Multivariate Phenotypic Data from Images" and "Selecting Experiments for Providing Response Paths" sections. Specifically, the features are the ten features listed near the end of the "Multivariate Phenotypic Data from Images" section collected for each of the six cell lines listed in the "Selecting Experiments for Providing Response Paths" section. In FIG. 3A, the connected data points link identical compounds at increasing concentration. Specifically, there were eight different concentrations for each compound.

Figure 3B:
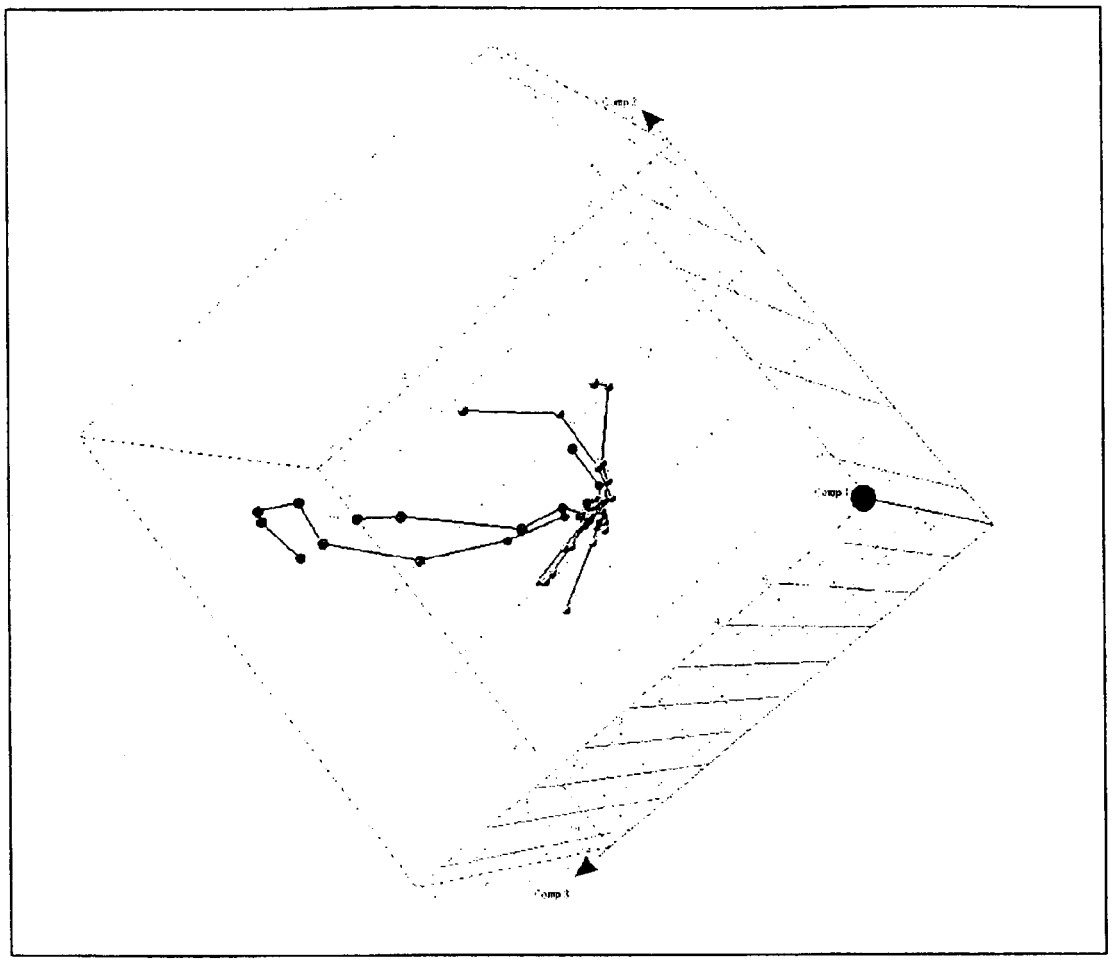
FIG. 3B is a plot of the dose response curves of only the farnesyltransferase and geranylgeranyltransferase inhibitors from FIG. 3A.

This dose-response path has proven to accurately classify different compound mechanisms. Even though many of the compound classes tested do not have a direct effect on the components/markers used in this experiment, quantitative phenotype paths are able to detect differences in this wide array of compounds. For example, there is a distinct separation of the farnesyltransferase and geranylgeranyltransferase inhibitors from each other even though both are involved in post-translational protein modification. These compounds are quite different from compounds that inhibit mitochondrial function (see FIG. 3B).

Figure 3C:
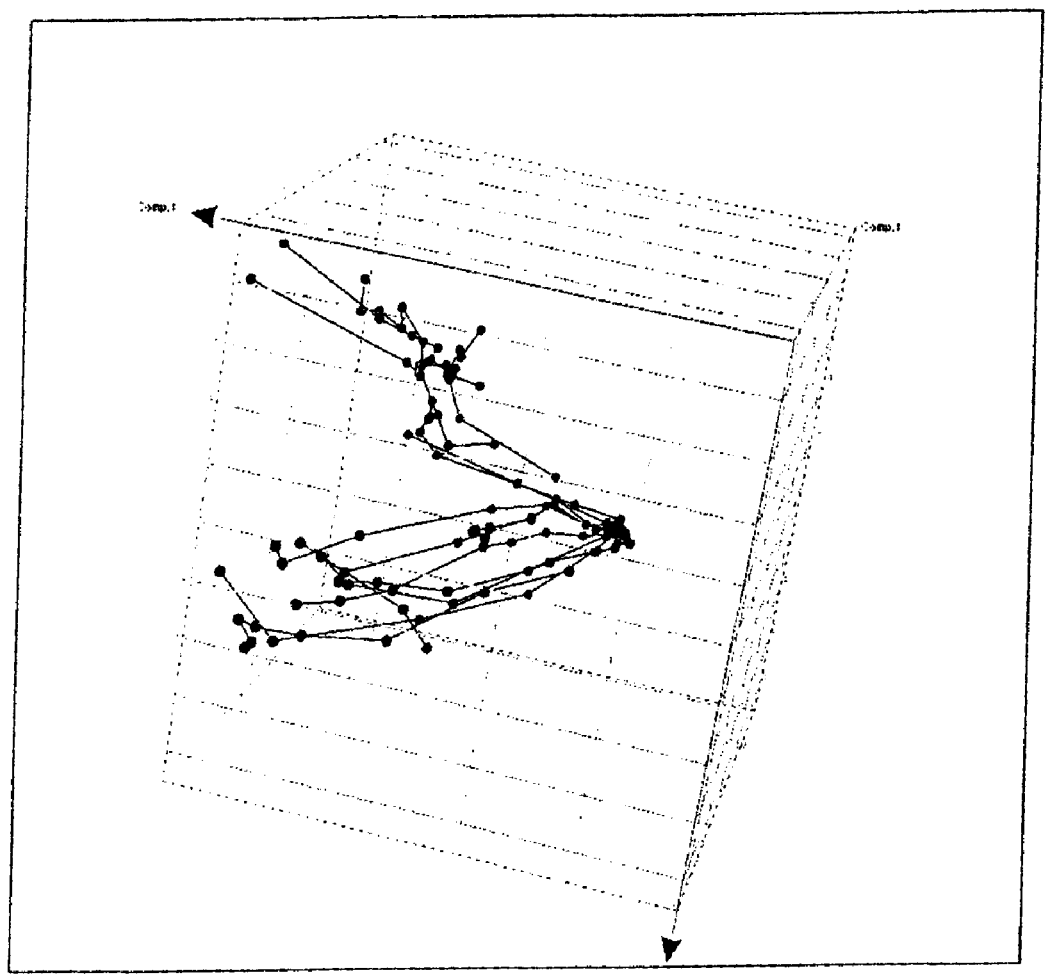
FIG. 3C is a plot of the dose response curves of only the actin and tubulin inhibitors from FIG. 3A.
Figure 3D:
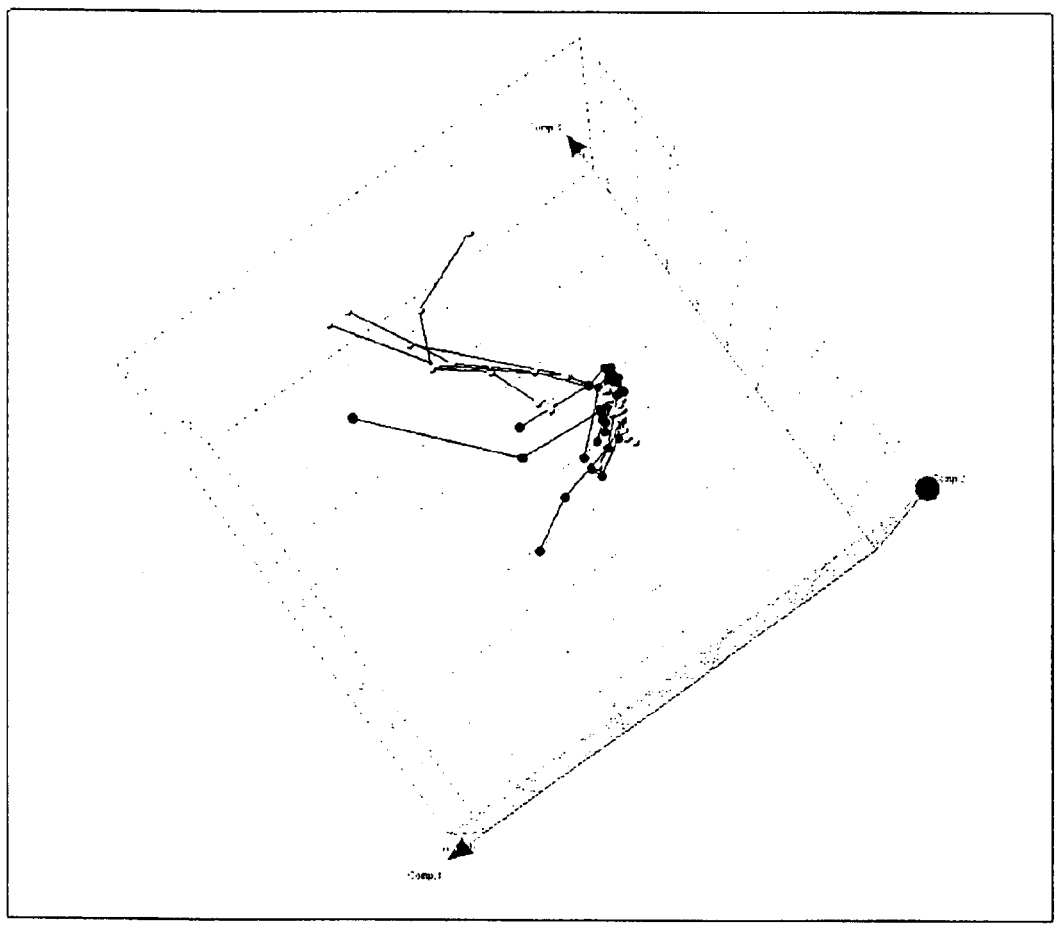
FIG. 3D is a plot of the dose response curves of only the compounds that effect signaling pathways directly from FIG. 3A.

Similarly, actin and tubulin inhibitors show distinct dose-response trajectories overall even though both classes affect the cytoskeleton (see FIG. 3C). Furthermore, compounds that effect signaling pathways directly, such as protein kinase inhibitors and calcium sensitizes, are uniquely differentiated from the other classes as well (see FIG. 3D).

The demonstration that many compound classes follow unique dose-response trajectories validates this invention's ability to measure the inhibition of many different types of targets by classifying a quantitative phenotype directly using a few carefully selected biological analyses. This information may be used to prioritize and expand marker sets, cell lines, and time-points used to generate the quantitative phenotypes. Further, it greatly increases the ability to resolve and differentiate ever more similar compound mechanisms.

Figure 4:
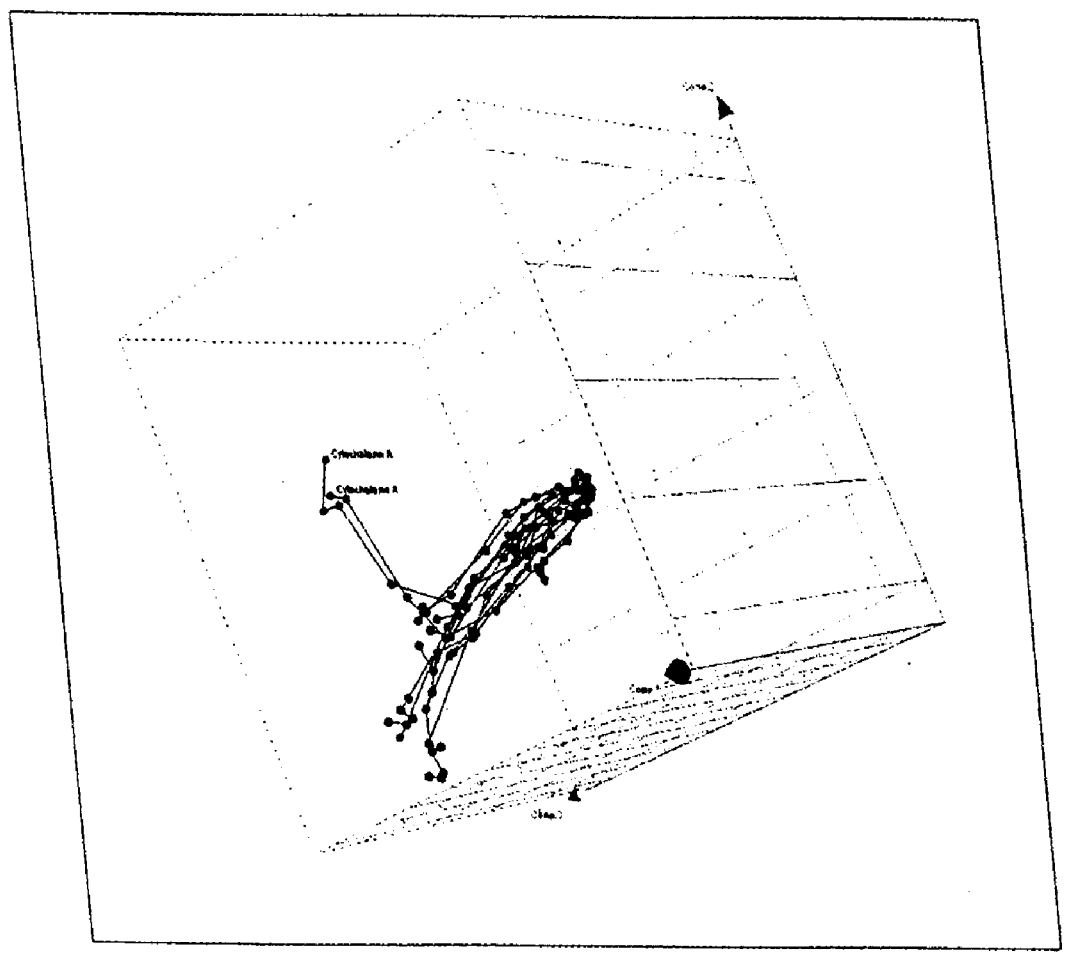
FIG. 4 is a PCA plot that highlights the deviation of the actin inhibitor Cytochalasin A from the other actin inhibitors.

Another example demonstrates the ability to investigate biological feature data (of the type used in the first example) to understand the differences and similarities between compounds. Despite the fact that the marker sets in this example did not include components of the actin cytoskeleton, the actin inhibitors are all uniquely classified by the quantitative phenotype paths. FIG. 4 highlights the deviation of the actin inhibitor Cytochalasin A from the other actin inhibitors. FIG. 4 also shows that the Cytochalasin A deviation is reliably reproduced when this experiment was run a second time.

To identify which biological features were changing in Cytochalasin A as the concentration of compound increased, biological feature image plots (not shown) for all cell lines and concentrations of two actin inhibitors were compared. The most significant difference in these image plots is the lack of an increase in the tubulin features at increasing concentrations of Cytochalasin A. All of the other actin inhibitors showed an increase in the tubulin biological features at the same concentrations (data not shown).

Figure 5A:
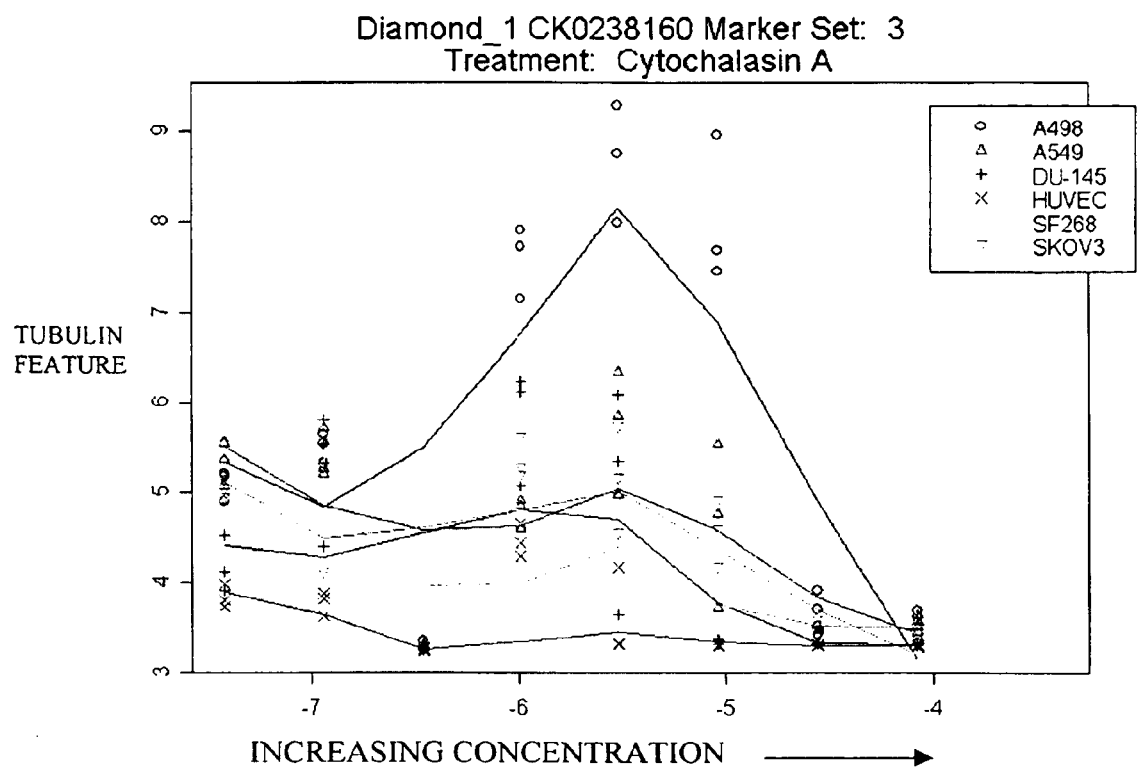
FIGS. 5A and 5B are plots of simple dose response curves of a tubulin feature as it varies with concentration of Cytochalasin A and Cytochalasin J, respectively.
Figure 5B:
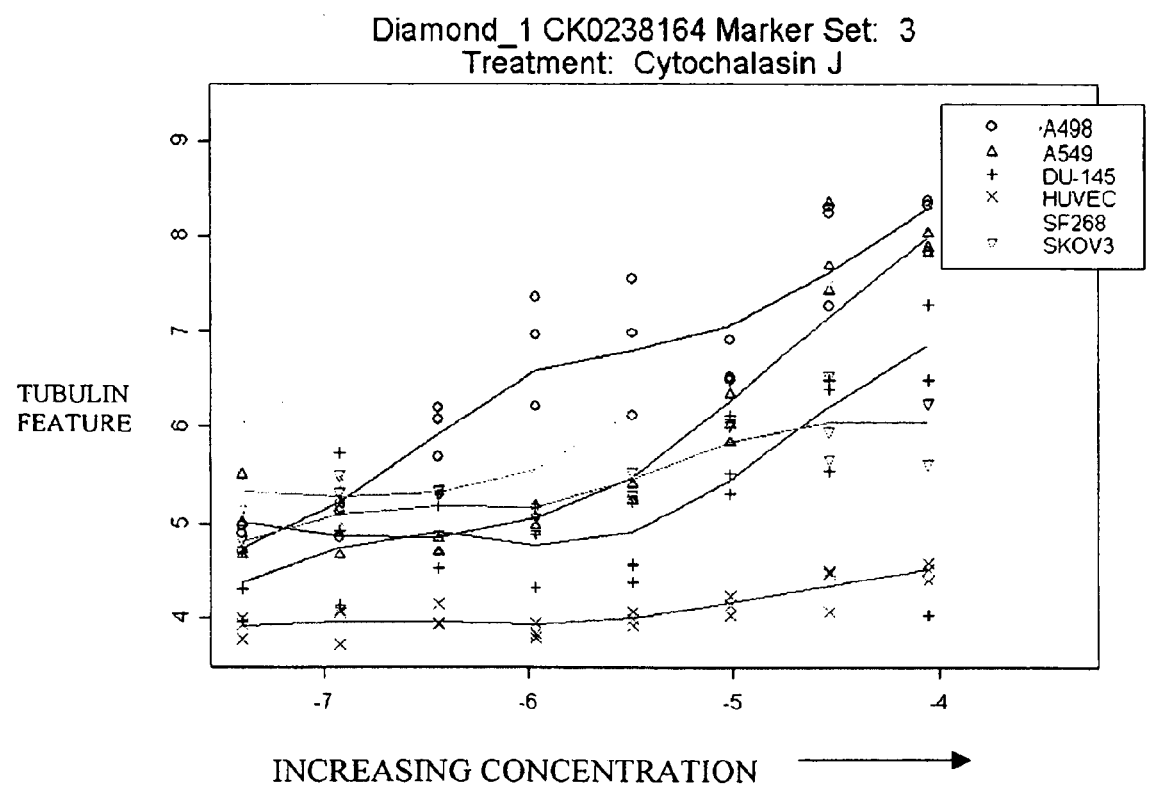

The change in the tubulin feature was further validated by inspection of the dose response graphs of all actin inhibitors for that feature across all cell lines and concentrations (see FIG. 5A (Cytochalasin A) and FIG. 5B (Cytochalasin J)) and inspection of a representative dose response image montages (not shown). (N.B. 18 different montages are available for 6 cell lines by 3 replicates.) Review of the literature confirmed that Cytochalasin A interferes with microtubule assembly by reacting with sulfhydryl groups. The data obtained with the present invention suggests that this side effect has a lower affinity than Cytochalasin A has for actin itself, as evident from the common PCA trajectory it shares with the rest of the actin inhibitors at lower concentrations.

Another way to review the data is to ask how similar the dose response paths are for different cell lines. These cell lines, with their different expression patterns, may exhibit increased or decreased sensitivity or off-target effects to different members within a single class of compounds. Because PCA analysis is only shedding light on the features that most distinguish compounds, an in depth cell-line sensitivity analysis may reveal more subtle differences and insight into molecular specificity.

Figure 6:
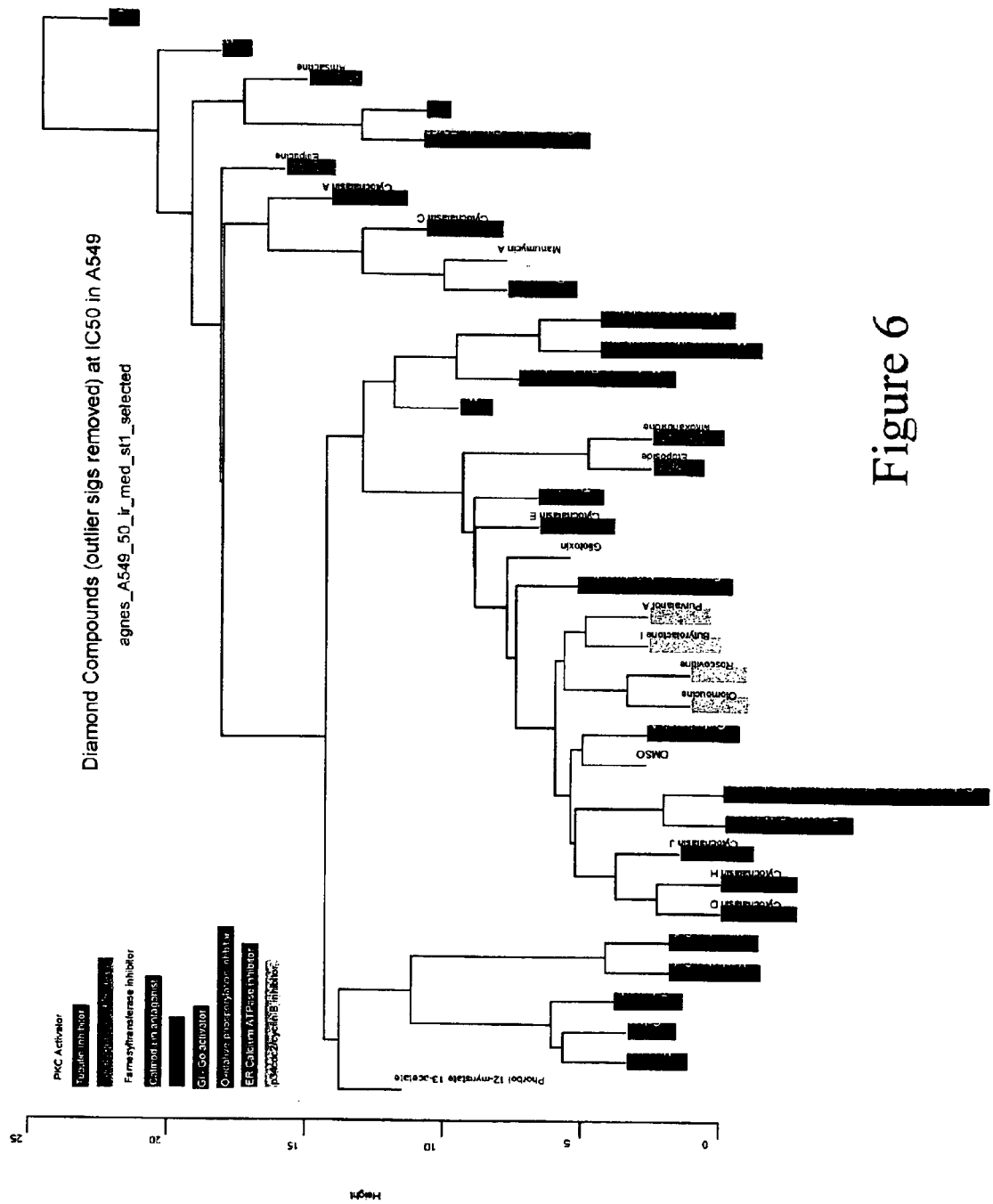
FIG. 6 is a dendrogram showing the compounds of FIG. 3A at the IC50 for A549 cells.

A way to visualize the similarities of compounds at biologically relevant concentration is to use hierarchical clustering. A dendrogram in FIG. 6 shows the compounds profiled at the IC50 for A549 cells. This visualization presents a different insight into compound mechanism than the PCA plot. For one, the p38cdc2/cyclinB inhibitors, the tubulin depolymerizers, and the G-protein activators are all highly correlated, while differences between the actin inhibitor molecules are highlighted. The biological features that are different can be visualized using an image plot of the same compounds in cluster order. This type of comparison can shed even more light into the biological similarities and differences between compounds at an even more subtle level.

Figure 7A:
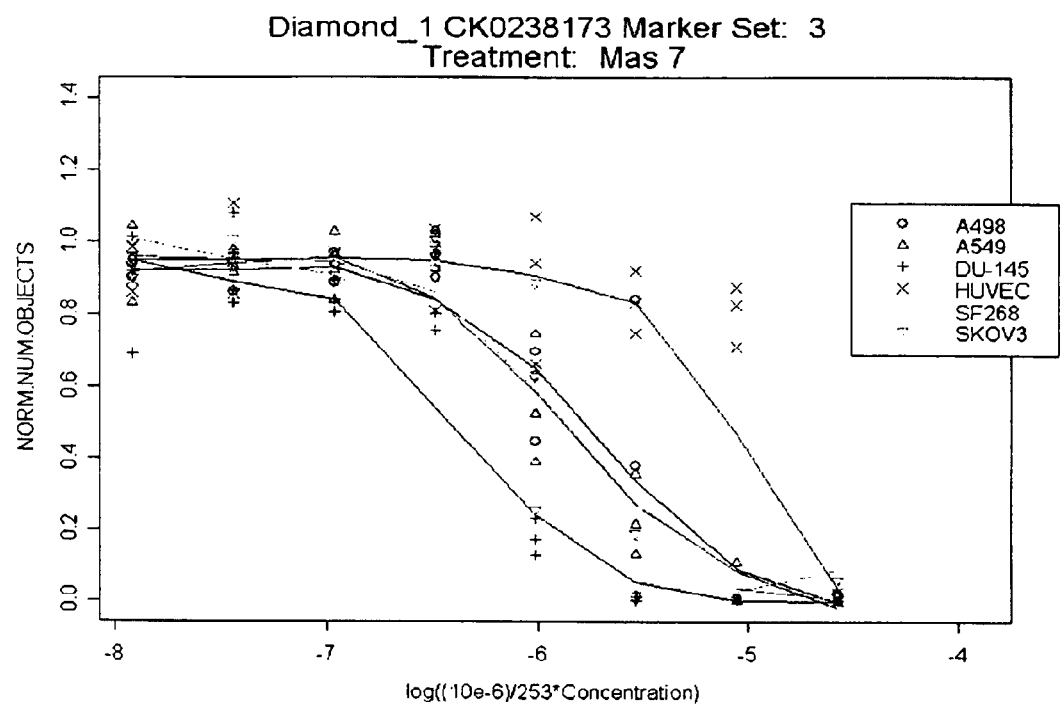
FIGS. 7A and 7B are plots of simple dose response curves, across cell lines, using cell count as indicator of the potency of Mastoparan and its synthetic analog MAS7, respectively.
Figure 7B:
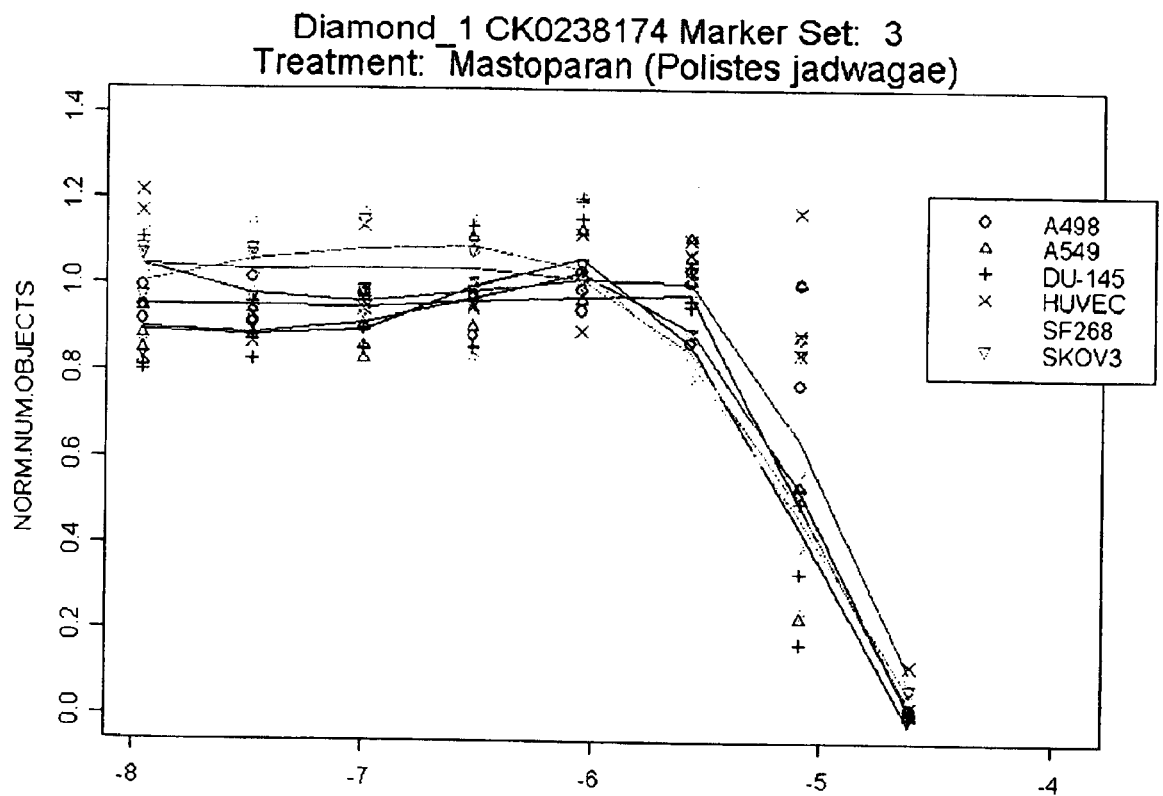

The effects of cell line sensitivity are apparent when one inspects the dose response graphs for a biological feature for all cell lines (see FIG. 7A). Mastoparan, an amphiphic wasp poison known to activate G proteins, and its analog tetradecapeptide derivative, MAS7 have very similar quantitative phenotype dose response profiles, as seen in the PCA plots (see FIG. 3D) and dendrogram (see FIG. 6) yet quite distinct cell line sensitivities (FIG. 7B). MAS7 is reported to have 5-fold greater potency than Mastoparan, but the dose response curves show that MAS7 is a more potent compound in the cancer cell lines; it does not exhibit increased sensitivity in the normal cell line. Further, the increase in potency is cell line dependent. The graphs of FIGS. 7A and 7B depict the decrease in the number of cells per image for each cell line as a function of concentration.

The oncology program Cytokinetics, Inc., South San Francisco, Calif. used the quantitative phenotyping technologies of this invention in a retrospective study to measure cellular phenotypes and biological effects of compounds that inhibit oncology program targets. In this effort, Cytokinetics' scientists submitted a series of 57 primary hits and optimized compounds against Oncology targets for profiling with this invention. The quantitative phenotyping of this invention identified a number of attractive chemical series against a validated target with a defined cellular morphological change expected from inhibiting the target. Quantitative phenotyping also identified compounds that exhibited off-target biological effects.

Figure 8:
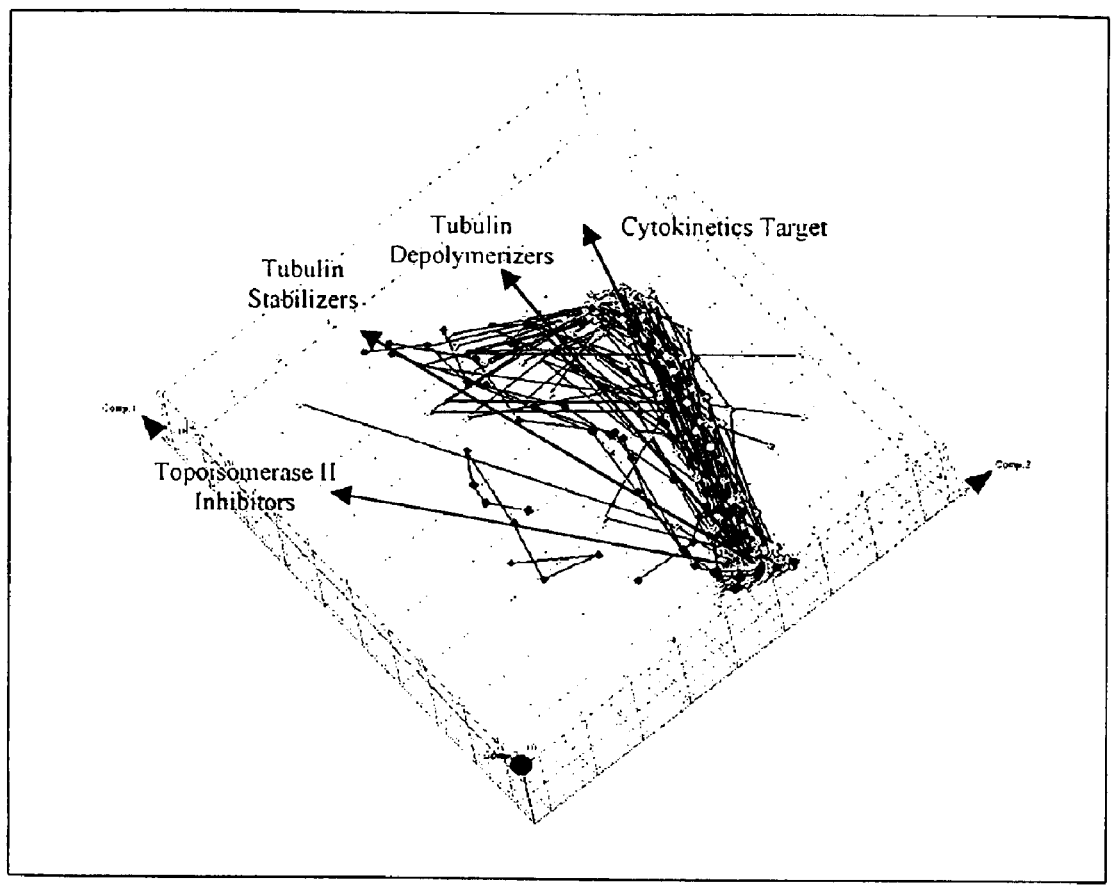
FIG. 8 is a PCA plot showing the dose response paths for 83 different oncology compounds clustered in groups representative of the mechanism of action.

Quantitative profiles of the oncology compounds were compared to a number of control compounds. Inspection of the quantitative profiles in principal component space revealed a significant and reproducible separation among the oncology targets, non-specific compounds, and controls. Notably, quantitative phenotyping differentiated compounds with similar biological effects, but different targets. FIG. 8 shows the dose response path (obtained as described in the examples above) taken by 83 different compounds clustered in groups representative of the mechanism of action. These paths connect identical compounds at increasing concentrations. Note that compounds that inhibit the Cytokinetics target are distinct from those that affect other cancer targets such as topoisomerase II, tubulin stabilizers, or tubulin depolymerizers.

Figure 9:
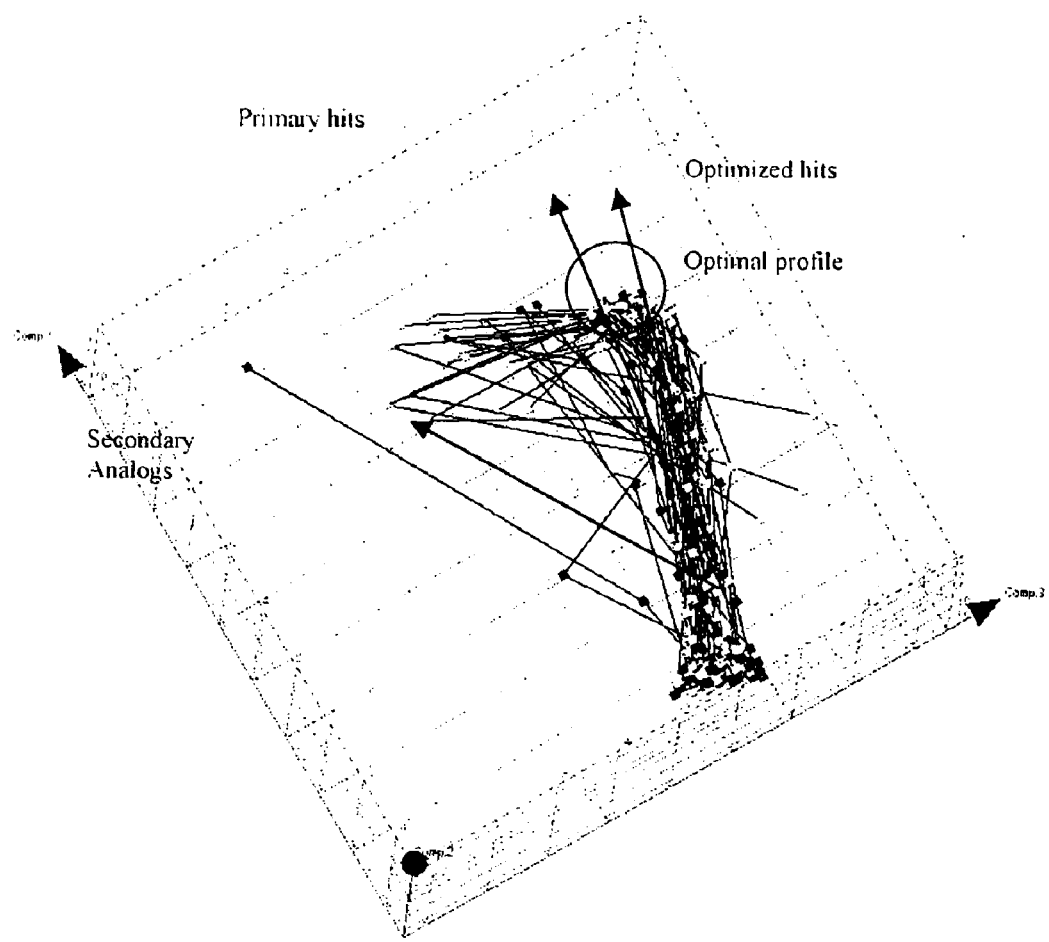
FIG. 9 is a PCA plot showing compounds that have biochemical activity against an oncology target described in the examples.
Figure 10:
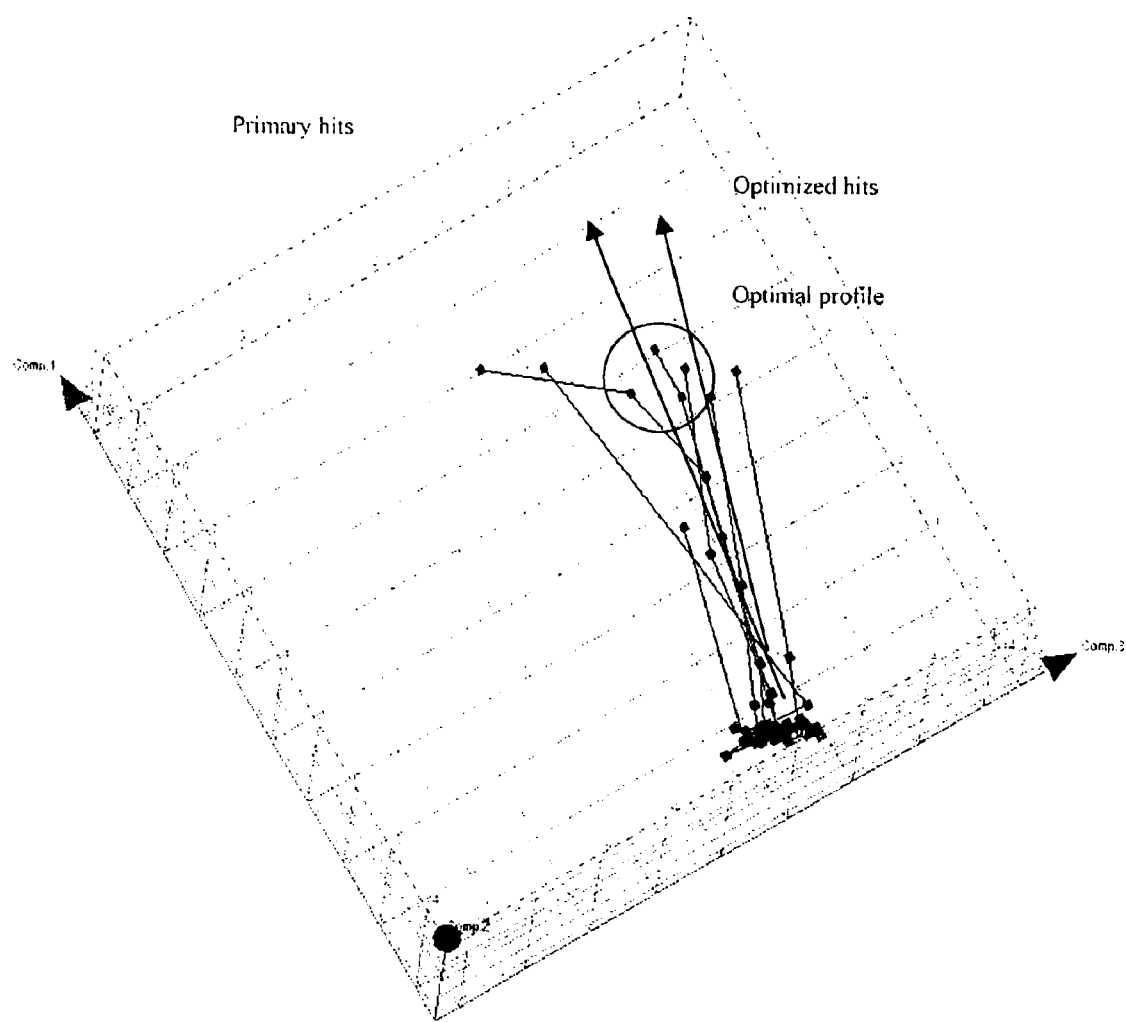
FIG. 10 is a PCA plot showing a subset of the compounds in FIG. 9, which subset was identified in a primary screen.

Most of the primary hits and early analogs from multiple chemical classes for one of the targets line up along a similar dose-response trajectory, while a few veer away (see FIGS. 9 and 10). This level of multivariate data group structurally unrelated compounds into groups with similar cellular phenotypes. Having this data available early in the drug discovery process allows the research scientist to know if structurally unrelated compounds cause a similar cellular phenotype which correlate to similar target selectivity, and to rapidly identify and reject compounds which correlate to off-target effects. The more compounds screened with the technologies of this invention, the clearer the distinctions become.

Figure 11:
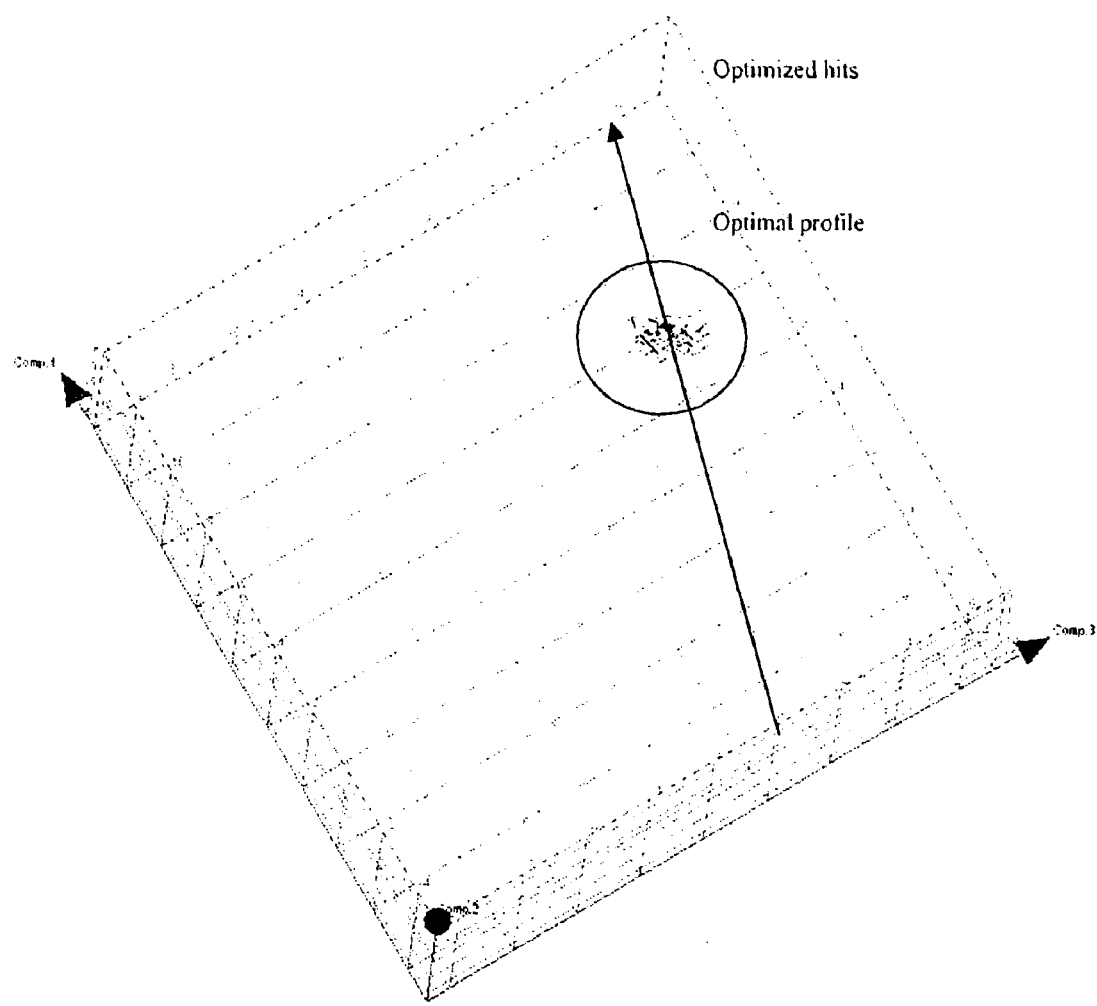
FIG. 11 is a plot showing a region of PCA space that represents the optimal profile for inhibition of an oncology target.

The optimized oncology compounds superimposed on the dose-response trajectory of the primary hits and formed a compact cluster of data points in one region of the graph that excluded other compounds (see FIG. 11). Inspection of the data and images revealed that the compounds in this region caused the morphological phenotype expected from inhibiting the target.

Figure 12:
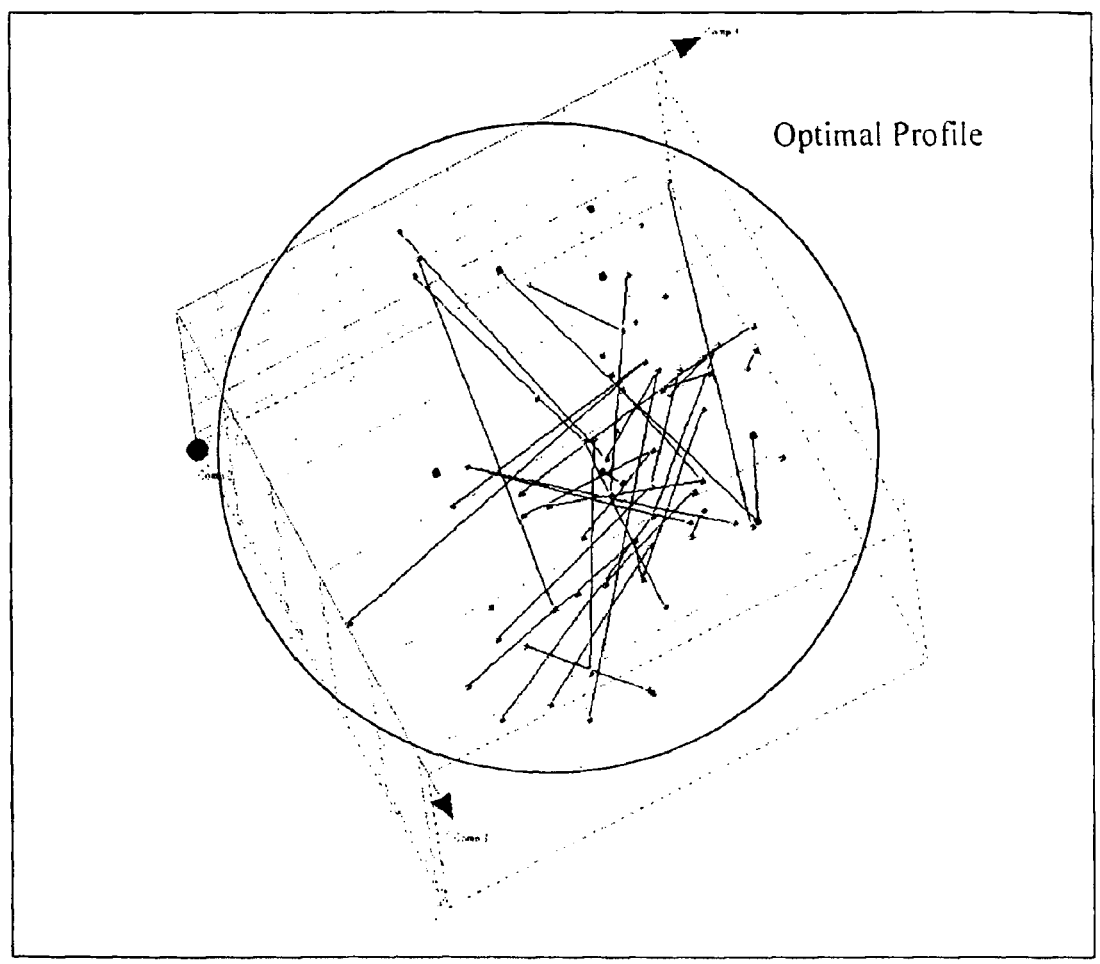
FIG. 12 is a zoomed-in figure of the compounds from FIG. 11 in PCA space.

This region was magnified to display each compound and concentration that caused the optimal profile (see FIG. 12). There were 39 compounds at many different concentrations showing that many of the chemical analogs have a similar profile. All compounds in the cluster are at concentrations lower than 10 micromolar. As one of the criteria for lead compound selection was potency, the number of compounds was further reduced to 8 by asking which compounds were able to produce the target specific profile at a delivered concentration of less than 40 nanomolar.

With the reduced data set, the biological feature data was further inspected to gain insight into the similarities and differences between these compounds. The compounds selected had a very distinct set of biological features that would have been almost impossible to predict in any other way. The differences between these compounds were further evaluated on a feature-by-feature level to provide further insight into the compounds' mechanism.

Figure 13:
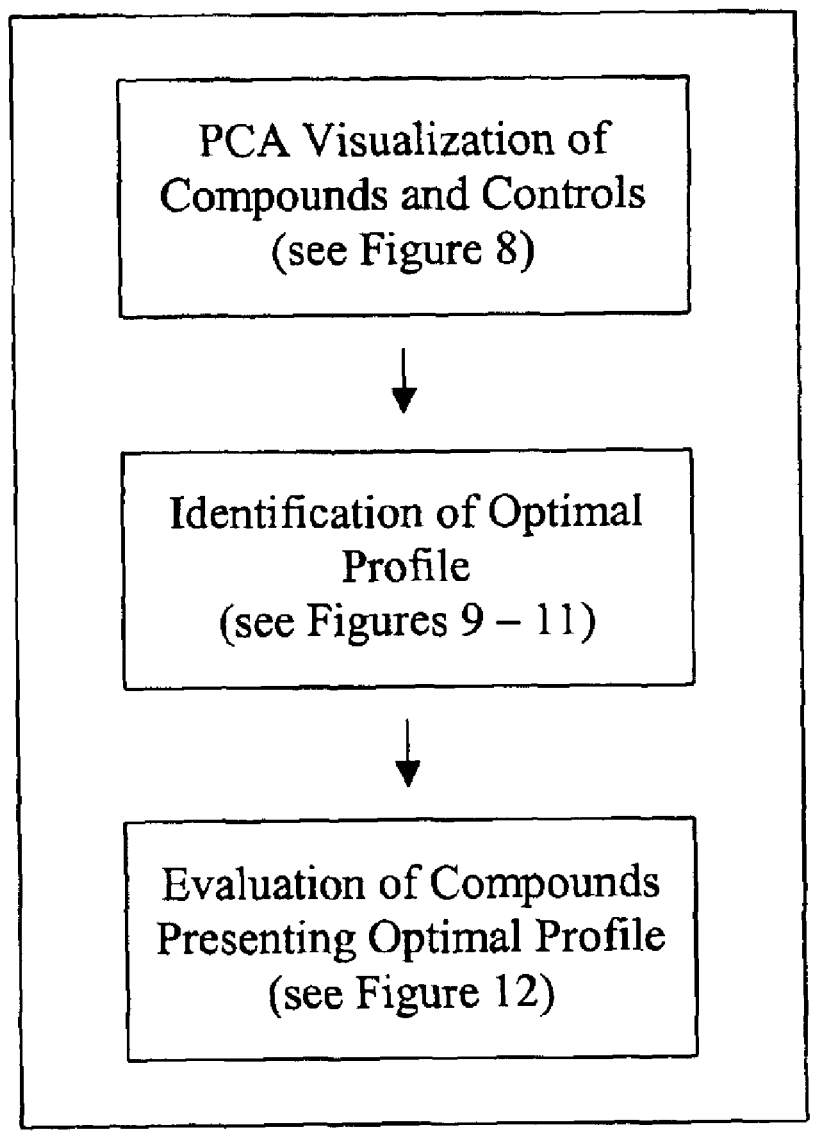
FIG. 13 is a process flow chart showing how a single multivariate dose response experiment was used to identify and narrow down 57 hits to eight highly potent and specific compounds.

FIG. 13 shows how a single multivariate dose response experiment was used to identify and narrow down 57 hits to eight highly potent and specific compounds. This demonstrates the breadth of information generated by present invention.

As a postscript, of the eight compounds shown in this example, four had been selected for extensive toxicity testing, and a derivative of one of those four was selected as a development compound. Going forward, the oncology program can use the profile information to select backup candidates for this target either by exploring the other four compounds identified, or profiling new compounds, and asking how similar they are to the optimal profile identified in this experiment.

CONCLUSION

Although the above has generally described the present invention according to specific processes and apparatus, the present invention has a much broader range of applicability. In particular, the present invention has been described in terms of cellular phenotypes that are derived primarily from image analysis, but is not so limited. Phenotypic stimulus response curves of this invention may contain data obtained primarily from non-image sources. Of course, one of ordinary skill in the art would recognize other variations, modifications, and alternatives.

What is claimed is:

1. A method for determining the response of cells to multiple levels of a stimulus, the method comprising: providing a 96-, 384-, or 1536-well plate, the wells of said plate containing a plurality of cells of different cell types, wherein at least some of said cells have been exposed to said stimulus;

for each of the multiple levels of a stimulus, obtaining a plurality of feature values from said cells of different cell types, wherein said feature values are obtained from images of said cells, wherein at least some of said feature values characterize the phenotype of cells exposed to the particular level of the stimulus, to thereby produce a separate quantitative phenotype of the cells at each level of stimulus; and identifying a path through the separate quantitative phenotypes of cells exposed to the stimulus, wherein points on the path represent quantitative phenotypes of said cells at different specified levels of the stimulus.

2. The method of claim 1, wherein the stimulus is selected from the group consisting of exposure to a chemical compound, exposure to a biological agent, exposure to electromagnetic radiation, exposure to particle radiation, exposure to an electrical or magnetic field or force, exposure to a mechanical field or force, and combinations thereof.

3. The method of claim 1, wherein the stimulus as exposure to a chemical agent.

4. The method of claim 1, further comprising comparing the path to a different path produced for a different stimulus to which cells were exposed at multiple levels.

5. The method of claim 1, wherein at least one of the feature values characterizes cell morphology.

6. The method of claim 1, wherein at least one of the feature values characterizes a statistical property of the cells.

7. The method of claim 1, wherein at least one of the feature values is a biological classification of the cells.

8. The method of claim 7, wherein the biological classification specifies a cell cycle state of the cells.

9. The method of claim 1, wherein the multiple levels of stimulus are multiple concentrations of a therapeutic or potential therapeutic.

10. The method of claim 1, further comprising presenting a graphical representation of the path.

11. The method of claim 10, wherein the graphical representation is provided along one or more principle components obtained via a principle component analysis.

12. The method of claim 1, further comprising providing quantitative phenotypes for each of multiple stimuli; and using all the quantitative phenotypes to provide a reduced-dimensionality space in with to depict the path.

13. The method of claim 1, wherein the multiple levels of stimulus are multiple times after an initial exposure to the stimulus.

14. A computer program product comprising a machine readable medium on which is provided program instructions for determining the response of a plurality of cells of a plurality of different cell types to multiple levels of a stimulus, the program instructions comprising:

program code for obtaining, for each of the multiple levels of stimulus, a plurality of feature values, at least some of which characterize the phenotype of cells exposed to the particular level of the stimulus to thereby produce a separate quantitative phenotype of the cells at each level of stimulus; and program code for identifying a path through the separate quantitative phenotypes of cells exposed to the stimulus, wherein points on the path represent quantitative phenotypes of said cells at different specified levels of the stimulus.

15. The computer program product of claim 14, wherein the stimulus is selected from the group consisting of exposure to a chemical compound, exposure to a biological agent, exposure to electromagnetic radiation, exposure to particle radiation, exposure to an electrical or magnetic field or force, exposure to a mechanical field or force, and combinations thereof.

16. The computer program product of claim 14, further comprising program instructions for comparing the path to a different path produced for a different stimulus to which cells were exposed at multiple levels.

17. The computer program product of claim 14, wherein at least some of the feature values are obtained from an image of the cells.

18. The computer program product of claim 14, wherein at least one of the feature values characterizes cell morphology.

19. The computer program product of claim 14, wherein at least one of the feature values characterizes a statistical property of the cells.

20. The computer program product of claim 14, wherein at least one of the feature values is a biological classification of the cells.

21. The computer product of claim 20, wherein the biological classification specifies a cell cycle state of the cells.

22. The computer program product of claim 14, further comprising program code for presenting a graphical representation of the path.

23. The computer program product of claim 22, wherein the graphical representation is provided along one or more principle components obtained via a principle component analysis.

24. The computer program product of claim 14, further comprising:

program code for providing quantitative phenotypes for each of multiple stimuli; and program code for using all the quantitative phenotypes to provide a reduced-dimensionally space in which to depict the path.

25. The computer program product of claim 14, wherein the multiple levels of stimulus are multiple times after an initial exposure to the stimulus.

26. The computer program product of claim 14, wherein the multiple levels of stimulus are multiple concentrations of a therapeutic or potential therapeutic.

27. A method for determining whether a first compound and a second compound act on cells by a related mechanism of action, the method comprising:

providing a 96-, 384-, or 1536-well plate, the wells of said plate containing a plurality of cells of a plurality of different cell types, wherein at least some of said cells have been exposed to multiple concentrations of said first compound or multiple concentrations of said second compound;

for each of multiple concentrations of the first compound, obtaining a plurality of feature values characterizing the phenotype of cells exposed to the particular concentration of the first compound, to thereby produce a plurality of first concentration-specific phenotypes;

identifying a first path through the first concentration-specific phenotypes of cells exposed to the first compound, wherein points on the first path represent quantitative phenotypes of said cells exposed to the first compound at different specified concentrations of the first compound;

for each of multiple concentrations of the second compound, obtaining a plurality of feature values characterizing the phenotype of cells exposed to the particular concentration of the second compound, to thereby produce a plurality of second concentration-specific phenotypes;

identifying a second path through second concentration-specific phenotypes of cells exposed to the second compound, wherein points on the second path represent quantitative phenotypes of said cells exposed to the second compound at different specified concentrations of the second compound; and comparing the first and second paths, wherein a degree of similarity between the paths corresponds to a degree of similarity in the mechanism of action of the first and second compounds.

28. The method of claim 27, wherein at least one of the first and second compounds is a known therapeutic or potential therapeutic.

29. The method of claim 27, wherein the multiple concentrations of the first compound vary from lowest to highest by a factor of at least about two.

30. The method of claim 27, wherein the multiple concentrations of the first compound include at least five separate concentrations of the first compound.

31. The method of claim 27, wherein the multiple concentrations of the first compound include at least eight separate concentrations of the first compound.

32. The method of claim 27, wherein obtaining a plurality of feature values characterizing the phenotype of cells exposed to the particular concentration of the first compound comprises analyzing images of a population of cells exposed to the particular concentration of the first compound.

33. The method of claim 27, wherein the plurality of feature values include numeric values characterizing one or more of the following cellular components: DNA, Golgi, cytoskeletal components, and the plasma membrane.

34. The method of claim 27, wherein the plurality of feature values include numeric values characterizing one or more of the following cellular components: DNA, Golgi, and tubulin.

35. The method of claim 27, wherein identifying the first path comprises analyzing the firs concentration-specific phenotypes via one or more of the following techniques: principal component analysis, linear and non-linear discriminant analysis, multidimensional scaling, and projection pursuit techniques.

36. The method of claim 27, wherein identifying the first path comprises analyzing the first concentration-specific phenotypes using principal component analysis.

37. The method of claim 27, wherein comparing the first and second paths comprises graphically depicting the first and second paths together.

38. The method of claim 27, wherein the graphical depiction presents the first and second paths in a space defined by principal components.

39. A computer program product comprising a machine readable medium on which is provided program instructions for determining whether a first compound and a second compound act on cells by a related mechanism of action, the program instructions comprising:

program code for obtaining, for each of multiple concentrations of the first compound, a plurality of feature values characterizing the phenotype of cells exposed to the particular concentration of the first compound to thereby produce a plurality of first concentration-specific phenotypes;

program code for identifying a first path through the first concentration-specific phenotypes of cells exposed to the first compounds, wherein points on the first path represent quantitative phenotypes of said cells exposed to the first compound at different specified concentrations of the first compound;

program code for obtaining, for each of multiple concentrations of the second compound, a plurality of feature values characterizing the phenotype of cells exposed to the particular concentration of the second compound to thereby produce a plurality of second concentration-specific phenotypes;

program code for identifying a second path through second concentration-specific phenotypes of cells exposed to the second compound, wherein points on the second path represent quantitative phenotypes of said cells exposed to the second compound at different specified concentrations of the second compound; and program code for comparing the first and second paths, wherein a degree of similarity between the paths corresponds to a degree of similarity in the mechanism of action of the first and second compounds.

40. The computer program product of claim 39, wherein at least one of the first and second compounds is a known therapeutic or potential therapeutic.

41. The computer program product of claim 39, wherein the program code for obtaining a plurality of feature values characterizing the phenotype of cells exposed to the particular concentration of the first compound comprises program code for analyzing images of a population of cells exposed to the particular concentration of the first compound.

42. The computer program product of claim 39, wherein the plurality of feature values include numeric values characterizing one or more of the following cellular components: DNA, Golgi, cytoskeletal components, and the plasma membrane.

43. The computer program product of claim 39, wherein the program code for identifying the first path comprises program code for analyzing the first concentration-specific phenotypes via one or more of the following techniques: principal component analysis, linear and non-linear discriminant analysis, multidimensional scaling, and projection pursuit techniques.

44. The computer program product of claim 39, wherein the program code for comparing the first and second paths comprises program code for graphically depicting the first and second paths together.

45. The computer program product of claim 44, wherein the graphical depiction presents the first and second paths in a space defined by principal components.

46. The computer program product of claim 39, wherein the plurality of feature values include numeric values characterizing one or more of the following cellular components: DNA, Golgi, and tubulin.

47. The computer program product of claim 39, wherein identifying the first path comprises analyzing the first concentration-specific phenotypes using principal component analysis.

* * * * *